US009373059B1

(12) United States Patent
Heifets et al.

(10) Patent No.: US 9,373,059 B1
(45) Date of Patent: Jun. 21, 2016

(54) SYSTEMS AND METHODS FOR APPLYING A CONVOLUTIONAL NETWORK TO SPATIAL DATA

(71) Applicant: Atomwise Inc., San Francisco, CA (US)

(72) Inventors: Abraham Samuel Heifets, San Francisco, CA (US); Izhar Wallach, Tel-Mond (IL); Michael Dzamba, San Francisco, CA (US)

(73) Assignee: ATOMWISE INC., San Francisco, CA (US)

( * ) Notice: Subject to any disclaimer, the term of this patent is extended or adjusted under 35 U.S.C. 154(b) by 0 days.

(21) Appl. No.: 15/050,983

(22) Filed: Feb. 23, 2016

Related U.S. Application Data

(63) Continuation-in-part of application No. PCT/CA2015/000296, filed on May 5, 2005.

(60) Provisional application No. 61/988,510, filed on May 5, 2014, provisional application No. 62/236,962, filed on Oct. 4, 2015.

(51) Int. Cl.
*G06K 9/62* (2006.01)
*G06K 9/66* (2006.01)
*G06N 3/08* (2006.01)
(Continued)

(52) U.S. Cl.
CPC *G06K 9/66* (2013.01); *G06F 19/16* (2013.01); *G06F 19/24* (2013.01); *G06K 9/52* (2013.01); *G06K 9/6267* (2013.01); *G06N 3/088* (2013.01); *G06T 1/20* (2013.01); *G06T 1/60* (2013.01); *G06T 7/60* (2013.01); *G06T 2200/04* (2013.01); *G06T 2200/28* (2013.01); *G06T 2207/20084* (2013.01)

(58) Field of Classification Search
None
See application file for complete search history.

(56) References Cited

U.S. PATENT DOCUMENTS 9,190,053 B2 11/2015 Penn et al.
9,202,144 B2 12/2015 Wang et al.
(Continued)

FOREIGN PATENT DOCUMENTS

WO WO 2015/168774 A1 11/2015

OTHER PUBLICATIONS

Wriggers, Willy, et al. "Topology representing neural networks reconcile biomolecular shape, structure, and dynamics." Neurocomputing 56 (2004): 365-379. 15 pages.*

(Continued)

*Primary Examiner* — Sumati Lefkowitz
*Assistant Examiner* — Ryan P Potts

(57) ABSTRACT

Systems and methods for test object classification are provided in which the test object is docked with a target object in a plurality of different poses to form voxel maps. The maps are vectorized and fed into a convolutional neural network comprising an input layer, a plurality of individually weighted convolutional layers, and an output scorer. The convolutional layers include initial and final layers. Responsive to vectorized input, the input layer feeds values into the initial convolutional layer. Each respective convolutional layer, other than the final convolutional layer, feeds intermediate values as a function of the weights and input values of the respective layer into another of the convolutional layers. The final convolutional layer feeds values into one or more fully connected layers as a function of the final layer weights and input values. The one or more full connected layers feed values into the scorer which scores each input vector to thereby classify the test object.

29 Claims, 22 Drawing Sheets

(51) Int. Cl.
  *G06T 1/20* (2006.01)
  *G06T 1/60* (2006.01)
  *G06K 9/52* (2006.01)
  *G06T 7/60* (2006.01)
  *G06F 19/16* (2011.01)
  *G06F 19/24* (2011.01)

(56) References Cited

U.S. PATENT DOCUMENTS

| | | | |
|---|---|---|---|
| 2002/0090631 A1 | 7/2002 | Gough et al. | |
| 2006/0034495 A1* | 2/2006 | Miller | G06K 9/00214 382/118 |
| 2013/0280238 A1 | 10/2013 | Evans et al. | |
| 2015/0238148 A1* | 8/2015 | Georgescu | A61B 5/7267 600/408 |
| 2015/0278441 A1* | 10/2015 | Min | G06N 99/005 706/12 |

OTHER PUBLICATIONS

Stahl, Martin, Chiara Taroni, and Gisbert Schneider. "Mapping of protein surface cavities and prediction of enzyme class by a self-organizing neural network." Protein engineering 13.2 (2000): 83-88. 6 pages.*

Fariselli, Piero, et al. "Prediction of protein-protein interaction sites in heterocomplexes with neural networks." European Journal of Biochemistry 269.5 (2002): 1356-1361. 6 pages.*

Nukada, Akira, et al. "High performance 3d convolution for protein docking on ibm blue gene." Parallel and Distributed Processing and Applications. Springer Berlin Heidelberg, 2007. 958-969. 12 pages.*

Clevert et al., 2014, "Rectified Factor Networks and Dropout," Deep Learning and Representation Learning Workshop, in conjunction with Neural Information Processing Systems (NIPS).

Da and Kireev, 2014, J. Chem. Inf. Model. 54, pp. 2555-2561, "Structural Protein-Ligand Interaction Fingerprints (SPLIF) for Structure-Based Virtual Screening: Method and Benchmark Study".

Kitchen et al. 2004, "Docking and scoring in virtual screening for drug discovery: methods and applications," Nat. Rev Drug Discov. 3, No. 11, pp. 935-949.

Krizhevsky et al., 2012, "ImageNet Classification with Deep Convolutional Neural Networks," in *Advances in Neural Information Processing Systems* 25 (NIPS 2012), eds. Pereira et al.

Morris et al., 2009, "AutoDock 4 and AutoDockTools4: Automated Docking with Selective Receptor Flexibility," in *J Compt Chem*. Dec. 2009; 30(16): 2785-2791.

Ramsundar et al., Feb. 6, 2015, "Massively Multitask Networks for Drug Discovery," arXiv:1502.02072v1.

Rarey et al., 1996, "A Fast Flexible docking Method using an Incremental Construction Algorithm," in *Journal of Molecular Biology* (1996) 261, pp. 470-489.

Unterthiner et al., 2014, "Deep Learning as an Opportunity in Virtual Screening," Deep Learning and Representation Learning Workshop, in conjunction with Neural Information Processing Systems (NIPS).

Unterthiner et al., Mar. 4, 2015, "Toxicity Prediction using Deep Learning," arXiv:1503.01445.

Wallach et al., Oct. 10, 2015, arXiv:1510.02855.1, "AtomNet: A Deep Convolutional Neural Network for Bioactivity Prediction in Structure-based Drug Discovery".

* cited by examiner

At a computer system 100 for classification of a test object 72 using spatial data, the computer system comprising a graphical processing unit 50 having a graphical processing memory 52, a general processor 74 and general memory 90 / 92 addressable by the general processing unit, the general memory storing at least one program 56 for execution by the at least one general processor, the at least one program obtains spatial coordinates 60 for a target object 58. ⟶ 202

The target object is a polymer. ⟶ 204

The polymer is a protein, a polypeptide, a polynucleic acid, a polyribonucleic acid, a polysaccharide, or an assembly of any combination thereof. ⟶ 206

The target object is a polymer and the spatial coordinates are a set of three-dimensional coordinates $\{x_1, ..., x_N\}$ for a crystal structure of the polymer resolved at a resolution of 2.5 Å or better. ⟶ 208

The target object is a polymer and the spatial coordinates are a set of three-dimensional coordinates $\{x_1, ..., x_N\}$ for a crystal structure of the polymer resolved at a resolution of 3.3 Å or better. ⟶ 210

The target object is a polymer and the spatial coordinates are an ensemble of three-dimensional coordinates of the polymer determined by nuclear magnetic resonance, neutron diffraction, or cryo-electron microscopy. ⟶ 212

Model the test objects 72 and/or training objects 66 with the target objects 58 in each pose of a plurality of different poses. ⟶ 214

The target object 58 is a polymer with an active site, the test object is a chemical compound, and the docking comprises docking the test object into the active site of the polymer. ⟶ 216

The plurality of different poses comprises 2 or more poses, 10 or more poses, 100 or more poses, or 1000 or more poses. ⟶ 218

The plurality of different poses are obtained by markup chain Monte Carlo sampling, simulated annealing, Lamarckian Genetic Algorithms, or genetic algorithms, using a docking scoring function. ⟶ 220

The plurality of different poses are obtained by incremental search using a greedy algorithm. ⟶ 222

Fig. 2A $$f(\vec{x_1}, \vec{x_2}, \ldots, \vec{x_{100}}) = g(g_0(\vec{x_1}, \vec{x_2}, \ldots, \vec{x_{100}}), g_1(\vec{x_1}, \vec{x_2}, \ldots, \vec{x_{100}}), \ldots, g_n(\vec{x_1}, \vec{x_2}, \ldots, \vec{x_{100}}))$$

$$\vec{x_1} = (x_1^1, x_1^2, \ldots, x_1^{40})$$

$$\vec{x_2} = (x_2^1, x_2^2, \ldots, x_2^{40})$$

SYSTEMS AND METHODS FOR APPLYING A CONVOLUTIONAL NETWORK TO SPATIAL DATA

CROSS REFERENCE TO RELATED APPLICATIONS

This application claims priority to International Patent Application No. PCT/CA2015/000296, entitled "Binding Affinity Prediction System and Method," filed May 5, 2015, which claims priority to U.S. Provisional Application No. 61/988,510, entitled "Binding Affinity Prediction System and Method," filed May 5, 2014, each of which is hereby incorporated by reference. This application also claims priority to U.S. Provisional Patent Application No. 62/236,962 entitled "Deep Convolutional Neural Network for Bioactivity Prediction in Structure Based Discovery," filed Oct. 4, 2015, which is hereby incorporated by reference.

TECHNICAL FIELD

This following relates generally to applying convolutional neural networks to spatial data.

BACKGROUND

Detecting structural motifs within three-dimensional spatial data of test objects docked onto target objects (complexes) that influence such docking is an important pattern recognition task, and has wide ranging applications, including, but not limited to the prediction the affinity of test objects to target objects. At the same time, detection of such structural motifs is hampered by uncertainties in the accuracy of the three-dimensional spatial data and uncertainty in the way test objects bind to target objects. For example, a given interaction between a test object and a target object can be affected by the distance, angle, atom type, charge and polarization, and surrounding stabilizing or destabilizing environmental factors involved.

The prior art include systems and methods that (i) are knowledge-based, (ii) are empirical, or (iii) include force-field based scoring functions. Knowledge-based features typically consist of counts of the number of times pairs of atoms or functional groups are separated by a given distance in complexes. Because these features are simple (two points separated by a distance), they are incapable of capturing the complex set of influencing factors described above. Empirical scoring functions fit a set of relative importance weights to a small number (few dozen) of hand-engineered features, such as the number of rotatable bonds, hydrogen bond donor-acceptor pairs, aromatic stacks, electrostatics, steric complementarity or strain, or solvent-accessible hydrophobic area. The development of these features requires expert knowledge and extensive manual tuning, yet any such feature will necessarily be a limited approximation since, as discussed above, the forces governing interactions between test objects and target objects cannot consistently be disentangled. Force-field based scoring functions are designed to be computationally efficient, which requires approximations to theoretical results from gas phase predictions. For example, such systems ignore or crudely approximate the important mediation of field strength by solvent.

Given the above background, there is a need for solutions that provide more accurate and/or more efficient detection of structural motifs within three-dimensional spatial data of complexes that influence the docking of test objects onto target objects.

SUMMARY

Systems and methods for test object classification are provided in which the test object is modeled with a target object in a plurality of different poses to form voxel maps. The voxel maps are vectorized and sequentially fed into a convolutional neural network. The convolutional neural network comprises an input layer, a plurality of individually weighted, sequentially connected convolutional layers, and an output scorer. The convolutional layers include an initial layer and a final layer. Responsive to vectorized input, the input layer feeds values into the initial convolutional layer. Each respective convolutional layer, other than the final convolutional layer, feeds intermediate values as a function of the weights of the respective convolutional layer and input values of the respective convolutional layer into another of the convolutional layers. The final convolutional layer feeds values into the scorer as a function of the final layer weights and input values. In this way, the scorer scores each of the input vector and these scores are collectively used to characterize the test object.

One aspect of the present disclosure provides a computer system which comprises a graphical processing unit having a graphical processing memory, a general processor, and general memory addressable by the general processing unit. The general memory stores at least one program for execution by the at least one general processor. The at least one program comprises instructions for obtaining a set of three-dimensional coordinates $\{x_1, \ldots, x_N\}$ for all or a portion of a target object (e.g., a polymer having an active site). Each respective $x_i$ in $\{x_1, \ldots, x_N\}$ is a three dimensional coordinate for an atom in a plurality of atoms in the target object. The at least one program further comprises instructions for modeling a test object (e.g., a chemical compound) with the target object (e.g., docking the test object into the active site of the target object in instances where the target object is a polymer) in each pose of a plurality of different poses, thereby creating a plurality of voxel maps. Each respective voxel map in the plurality of voxel maps comprises the target object (e.g., the active site of the target object) and the test object in a respective pose in the plurality of different poses. The at least one program further comprises instructions for unfolding each voxel map in the plurality of voxel maps into a corresponding vector, thereby creating a plurality of vectors. In some embodiments, each such vector in the plurality of vectors is the same size. In some embodiments, each such vector is a different size. In some embodiments the voxels are not vectorized. The at least one program further comprises instructions for providing the plurality of vectors to the graphical processing unit (GPU) memory, where the GPU memory includes a network architecture (convolutional neural network) that includes an input layer for receiving the plurality of vectors one at a time, a plurality of convolutional layers, and a scorer. The plurality of convolutional layers includes an initial convolutional layer and a final convolutional layer. Each layer in the plurality of convolutional layers is associated with a different set of weights. In some embodiments the above-described network architecture that includes an input layer for receiving the plurality of vectors one at a time, a plurality of convolutional layers, and a scorer is stored in general random access memory, not GPU memory. In some embodiments, the voxels are not vectorized but are fed directly into the convolutional neural network.

In some embodiments, the scorer comprises a decision tree, a multiple additive regression tree, a clustering algorithm, principal component analysis, a nearest neighbor analysis, a linear discriminant analysis, a quadratic discriminant analysis, a support vector machine, an evolutionary method, a projection pursuit, or ensembles thereof.

Responsive to input of a respective vector in the plurality of vectors (or the respective vector directly), the input layer feeds a first plurality of values into the initial convolutional layer as a first function of values in the respective vector. In some embodiments, the first function is computed using the GPU. In some embodiments it is not. Each respective convolutional layer, other than the final convolutional layer, feeds intermediate values, as a respective second function of (i) the different set of weights associated with the respective convolutional layer and (ii) input values received by the respective convolutional layer, into another convolutional layer in the plurality of convolutional layers. In some embodiments, the second function is computed using the GPU. In some embodiments it is not. The final convolutional layer feeds final values, as a third function of (i) the different set of weights associated with the final convolutional layer and (ii) input values received by the final convolutional layer into the scorer. The at least one program further comprises instructions for obtaining a plurality of scores from the scorer, where each score in the plurality of scores corresponds to the input of a vector in the plurality of vectors (or a corresponding voxel map) into the input layer. The plurality of scores is used to determine a classification of the test object. In some embodiments, a weighted average of the plurality of scores is used to determine a classification of the test object.

Another aspect of the present disclosure provides a computer system for test object evaluation. The computer system optionally comprises a graphical processing unit (GPU) having a GPU memory. The computer further includes a general processor and general memory addressable by the general processing unit. In some embodiments the GPU memory comprises a convolutional neural network. In some alternative embodiments the general memory comprises the convolutional neural network. The general memory stores at least one program for execution by the at least one general processor. The at least one program comprises instructions for obtaining, using the general processor, a first data file from a first memory location in the general memory. The first data file comprises a set of three-dimensional coordinates $\{x_1, \ldots, x_N\}$ for all or a portion of a target object (e.g., a polymer having an active site), where each respective $x_i$ in $\{x_1, \ldots, x_N\}$ is a three dimensional coordinate for an atom in a plurality of atoms in the target object. The at least one program further comprises instructions for modeling a test object (e.g., a chemical compound) with the target object (e.g., docking the test object into an active site of the target object) in each of a plurality of different poses, thereby creating a plurality of poses for the target object. The at least one program further comprises instructions for creating a plurality of voxel maps, where each respective voxel map in the plurality of voxel maps is created by a method comprising (i) sampling the test object, in a respective pose in the plurality of different poses, and a portion of the target object that is contact with the test object in the respective pose (e.g., the active site of the target object in instance where the target object is a polymer) on a three-dimensional basis (e.g., grid basis) thereby forming a corresponding three dimensional space filling uniform honeycomb comprising a corresponding plurality of three-dimensional space filling polyhedral cells. For each respective three-dimensional cell in the corresponding plurality of three-dimensional cells, a voxel in the respective voxel map is populated based upon one or more properties (e.g., chemical properties such as distance, angle, atom type, charge and polarization, and surrounding stabilizing or destabilizing environmental factors) of the respective three-dimensional cell. The at least one program further comprises instructions for applying, optionally using the graphical processing unit, each voxel map in the plurality of voxel maps to the convolutional neural network thereby obtaining a plurality of scores for the test object. The at least one program further comprises instructions for combining the plurality scores to derive a composite score for the chemical compound, where the composite score indicates a binding affinity of the test object to the target object.

BRIEF DESCRIPTION OF THE DRAWINGS

In the drawings, embodiments of the systems and method of the present disclosure are illustrated by way of example. It is to be expressly understood that the description and drawings are only for the purpose of illustration and as an aid to understanding, and are not intended as a definition of the limits of the systems and methods of the present disclosure.

FIGS. 2A, 2B, 2C, 2D, 2E and 2F illustrate computer systems and methods for applying a convolutional neural network to spatial data in accordance with some embodiments.

FIG. 14 is a depiction of applying multiple function computation elements (g1, g2, . . . ) to the voxel inputs (x1, x2, . . . , x100) and composing the function computation element outputs together using g( ) according to an embodiment.

Like reference numerals refer to corresponding parts throughout the several views of the drawings.

DETAILED DESCRIPTION

Figure 1:
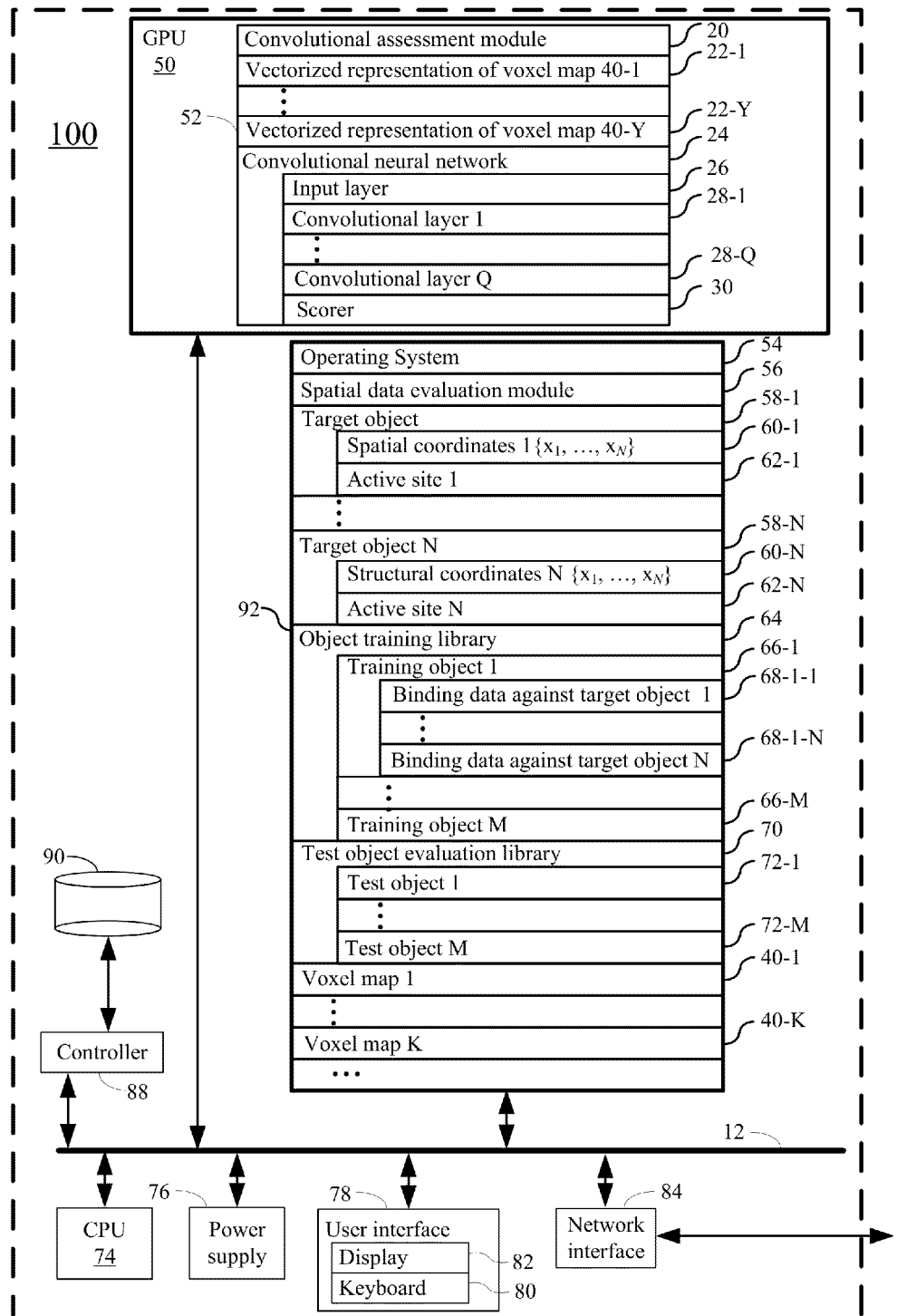
FIG. 1 illustrates a computer system that applies a convolutional neural network to spatial data in accordance with some embodiments.

Reference will now be made in detail to embodiments, examples of which are illustrated in the accompanying drawings. In the following detailed description, numerous specific details are set forth in order to provide a thorough understanding of the present disclosure. However, it will be apparent to one of ordinary skill in the art that the present disclosure may be practiced without these specific details. In other instances, well-known methods, procedures, components, circuits, and networks have not been described in detail so as not to unnecessarily obscure aspects of the embodiments.

It will also be understood that, although the terms first, second, etc. may be used herein to describe various elements, these elements should not be limited by these terms. These terms are only used to distinguish one element from another. For example, a first subject could be termed a second subject, and, similarly, a second subject could be termed a first subject, without departing from the scope of the present disclosure. The first subject and the second subject are both subjects, but they are not the same subject.

The terminology used in the present disclosure is for the purpose of describing particular embodiments only and is not intended to be limiting of the invention. As used in the description of the invention and the appended claims, the singular forms "a", "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting [the stated condition or event]" or "in response to detecting [the stated condition or event]," depending on the context.

The present disclosure provides systems and methods for test object classification. A test object is docked with a target object in a plurality of different energetically acceptable binding modes, termed poses, to form a corresponding plurality of voxel maps. An example of a target object is a polymer with an active site and an example of a test object is a compound that may or may not bind to the active site with appreciative affinity. In some embodiments, the voxel maps are vectorized and sequentially fed into a convolutional neural network. In some embodiments, the voxel maps are directly sequentially fed into a convolutional neural network without vectorization. In some embodiments, each such voxel map represents the pose of the test object in relation to the target object. For instance, in some embodiments, each voxel map represents a compound that is bound in a different orientation in the active site of the polymer. The convolutional neural network comprises an input layer, a plurality of individually weighted convolutional layers, and an output scorer. The convolutional layers include an initial layer and a final layer. Responsive to input, the input layer feeds values into the initial convolutional layer. Each respective convolutional layer, other than the final convolutional layer, feeds intermediate values as a function of the weights of the respective convolutional layer and input values of the respective convolutional layer into another of the convolutional layers. The final convolutional layer feeds values into the scorer as a function of the final layer weights and input values. In this way, the scorer scores each of the input vectors (or input voxel maps) and these scores are collectively used to classify the test object. In some embodiments, the scorer provides a single score for each of the input vectors (or input voxel maps) and the weighted average of these scores is used to classify the test object.

FIG. 1 illustrates a computer system 100 that applies the above-described convolutional neural network to spatial data. For instance, it can be used as a binding affinity prediction system to generate accurate predictions regarding the binding affinity of one or more test objects (e.g., chemical compounds) with a set of one or more target objects (e.g., polymers).

Referring to FIG. 1, in typical embodiments, analysis computer system 100 comprises one or more computers. For purposes of illustration in FIG. 1, the analysis computer system 100 is represented as a single computer that includes all of the functionality of the disclosed analysis computer system 100. However, the disclosure is not so limited. The functionality of the analysis computer system 100 may be spread across any number of networked computers and/or reside on each of several networked computers. One of skill in the art will appreciate that a wide array of different computer topologies are possible for the analysis computer system 100 and all such topologies are within the scope of the present disclosure.

Turning to FIG. 1 with the foregoing in mind, an analysis computer system 100 comprises one or more processing units (CPU's) 74, a network or other communications interface 84, a user interface (e.g., including a display 82 and keyboard 80 or other form of input device) a memory 92 (e.g., random access memory), one or more magnetic disk storage and/or persistent devices 90 optionally accessed by one or more controllers 88, one or more communication busses 12 for interconnecting the aforementioned components, and a power supply 76 for powering the aforementioned components. Data in memory 92 can be seamlessly shared with non-volatile memory 90 using known computing techniques such as caching. Memory 92 and/or memory 90 can include mass storage that is remotely located with respect to the central processing unit(s) 74. In other words, some data stored in memory 92 and/or memory 90 may in fact be hosted on computers that are external to analysis computer system 100 but that can be electronically accessed by the analysis computer system over an Internet, intranet, or other form of network or electronic cable using network interface 84. In some embodiments, the analysis computer system 100 makes use of a convolutional neural network that is run from the memory 52 associated with one or more graphical processing units 50 in order to improve the speed and performance of the system. In some alternative embodiments, the analysis computer system 100 makes use of a convolutional neural network that is run from memory 92 rather than memory associated with a graphical processing unit 50.

The memory 92 of analysis computer system 100 stores:
- an operating system 54 that includes procedures for handling various basic system services;
- a spatial data evaluation module 56 for evaluating spatial data such as the binding of test objects (or training objects) to target objects;
- data for one or more target object 58, including structural data 60 and optionally active site information 62;
- an object training library 64 that includes binding data 68 against target objects 58 for each of a plurality of training objects 66;
- a test object evaluation library 70 that comprises information for a plurality of test objects 72; and a plurality of voxel maps 40, each voxel map representing the pose of a training object 66 or test object 72 against a target object 58;

The memory 52, or optionally memory 92, of analysis computer system 100 stores:

a convolutional assessment module 20 for applying convolutional neural networks to spatial data (e.g., for applying a convolutional neural network to test or training object docked onto target objects);

one or more (optionally) vectorized 22 representations of voxel maps 40; and a convolutional neural network 24 that includes an input layer 26, one or more convolutional layers 28, and a terminal scorer 30.

In some implementations, one or more of the above identified data elements or modules of the analysis computer system 100 are stored in one or more of the previously mentioned memory devices, and correspond to a set of instructions for performing a function described above. The above identified data, modules or programs (e.g., sets of instructions) need not be implemented as separate software programs, procedures or modules, and thus various subsets of these modules may be combined or otherwise re-arranged in various implementations. In some implementations, the memory 92 and/or 90 (and optionally 52) optionally stores a subset of the modules and data structures identified above. Furthermore, in some embodiments the memory 92 and/or 90 (and optionally 52) stores additional modules and data structures not described above.

Now that a system for evaluation of the docking of test or training objects onto target object using spatial data has been disclosed, methods for performing such evaluation is detailed with reference to FIG. 2 and discussed below.

Obtaining Spatial Coordinates for a Target Object 202.

In accordance with FIG. 2 methods are performed at or with a computer system 100 for classification of a test object 72 (or training object) using spatial data. The computer system 100 optionally comprises a graphical processing unit 50 having a graphical processing memory 52. The computer system 100 comprises a general processor 74 and general memory 90/92 addressable by the general processing unit. The general memory stores at least one program 56 for execution by the at least one general processor. The at least one program obtains spatial coordinates 60 for a target object 58.

In some embodiments, the target object 58 is a polymer (204). Examples of polymers include, but are not limited to, proteins, polypeptides, polynucleic acids, polyribonucleic acids, polysaccharides, or assemblies of any combination thereof (206). A polymer, such as those studied using some embodiments of the disclosed systems and methods, is a large molecule composed of repeating residues. In some embodiments, the polymer is a natural material. In some embodiments, the polymer is a synthetic material. In some embodiments, the polymer is an elastomer, shellac, amber, natural or synthetic rubber, cellulose, Bakelite, nylon, polystyrene, polyethylene, polypropylene, polyacrylonitrile, polyethylene glycol, or a polysaccharide.

In some embodiments, the target object 58 is a heteropolymer (copolymer). A copolymer is a polymer derived from two (or more) monomeric species, as opposed to a homopolymer where only one monomer is used. Copolymerization refers to methods used to chemically synthesize a copolymer. Examples of copolymers include, but are not limited to, ABS plastic, SBR, nitrile rubber, styrene-acrylonitrile, styrene-isoprene-styrene (SIS) and ethylene-vinyl acetate. Since a copolymer consists of at least two types of constituent units (also structural units, or particles), copolymers can be classified based on how these units are arranged along the chain. These include alternating copolymers with regular alternating A and B units. See, for example, Jenkins, 1996, "Glossary of Basic Terms in Polymer Science," Pure Appl. Chem. 68 (12): 2287-2311, which is hereby incorporated herein by reference in its entirety. Additional examples of copolymers are periodic copolymers with A and B units arranged in a repeating sequence (e.g. (A-B-A-B-B-A-A-A-A-B-B-B)$_n$). Additional examples of copolymers are statistical copolymers in which the sequence of monomer residues in the copolymer follows a statistical rule. See, for example, Painter, 1997, *Fundamentals of Polymer Science*, CRC Press, 1997, p 14, which is hereby incorporated by reference herein in its entirety. Still other examples of copolymers that may be evaluated using the disclosed systems and methods are block copolymers comprising two or more homopolymer subunits linked by covalent bonds. The union of the homopolymer subunits may require an intermediate non-repeating subunit, known as a junction block. Block copolymers with two or three distinct blocks are called diblock copolymers and triblock copolymers, respectively.

In some embodiments, the target object 58 is in fact a plurality of polymers, where the respective polymers in the plurality of polymers do not all have the same molecular weight. In some such embodiments, the polymers in the plurality of polymers fall into a weight range with a corresponding distribution of chain lengths. In some embodiments, the polymer is a branched polymer molecule comprising a main chain with one or more substituent side chains or branches. Types of branched polymers include, but are not limited to, star polymers, comb polymers, brush polymers, dendronized polymers, ladders, and dendrimers. See, for example, Rubinstein et al., 2003, *Polymer physics*, Oxford; New York: Oxford University Press. p. 6, which is hereby incorporated by reference herein in its entirety.

In some embodiments, the target object 58 is a polypeptide. As used herein, the term "polypeptide" means two or more amino acids or residues linked by a peptide bond. The terms "polypeptide" and "protein" are used interchangeably herein and include oligopeptides and peptides. An "amino acid," "residue" or "peptide" refers to any of the twenty standard structural units of proteins as known in the art, which include imino acids, such as proline and hydroxyproline. The designation of an amino acid isomer may include D, L, R and S. The definition of amino acid includes nonnatural amino acids. Thus, selenocysteine, pyrrolysine, lanthionine, 2-aminoisobutyric acid, gamma-aminobutyric acid, dehydroalanine, ornithine, citrulline and homocysteine are all considered amino acids. Other variants or analogs of the amino acids are known in the art. Thus, a polypeptide may include synthetic peptidomimetic structures such as peptoids. See Simon et al., 1992, Proceedings of the National Academy of Sciences USA, 89, 9367, which is hereby incorporated by reference herein in its entirety. See also Chin et al., 2003, Science 301, 964; and Chin et al., 2003, Chemistry & Biology 10, 511, each of which is incorporated by reference herein in its entirety.

The target objects 58 evaluated in accordance with some embodiments of the disclosed systems and methods may also have any number of posttranslational modifications. Thus, a target object includes those polymers that are modified by acylation, alkylation, amidation, biotinylation, formylation, γ-carboxylation, glutamylation, glycosylation, glycylation, hydroxylation, iodination, isoprenylation, lipoylation, cofactor addition (for example, of a heme, flavin, metal, etc.), addition of nucleosides and their derivatives, oxidation, reduction, pegylation, phosphatidylinositol addition, phosphopantetheinylation, phosphorylation, pyroglutamate formation, racemization, addition of amino acids by tRNA (for example, arginylation), sulfation, selenoylation, ISGylation, SUMOylation, ubiquitination, chemical modifications (for example, citrullination and deamidation), and treatment with other enzymes (for example, proteases, phosphotases and kinases). Other types of posttranslational modifications are known in the art and are also included.

In some embodiments, the target object 58 is an organometallic complex. An organometallic complex is chemical compound containing bonds between carbon and metal. In some instances, organometallic compounds are distinguished by the prefix "organo-" e.g. organopalladium compounds.

In some embodiments, the target object 58 is a surfactant. Surfactants are compounds that lower the surface tension of a liquid, the interfacial tension between two liquids, or that between a liquid and a solid. Surfactants may act as detergents, wetting agents, emulsifiers, foaming agents, and dispersants. Surfactants are usually organic compounds that are amphiphilic, meaning they contain both hydrophobic groups (their tails) and hydrophilic groups (their heads). Therefore, a surfactant molecule contains both a water insoluble (or oil soluble) component and a water soluble component. Surfactant molecules will diffuse in water and adsorb at interfaces between air and water or at the interface between oil and water, in the case where water is mixed with oil. The insoluble hydrophobic group may extend out of the bulk water phase, into the air or into the oil phase, while the water soluble head group remains in the water phase. This alignment of surfactant molecules at the surface modifies the surface properties of water at the water/air or water/oil interface.

Examples of ionic surfactants include ionic surfactants such as anionic, cationic, or zwitterionic (ampoteric) surfactants. In some embodiments, the target object 58 is a reverse micelle or liposome.

In some embodiments, the target object 58 is a fullerene. A fullerene is any molecule composed entirely of carbon, in the form of a hollow sphere, ellipsoid or tube. Spherical fullerenes are also called buckyballs, and they resemble the balls used in association football. Cylindrical ones are called carbon nanotubes or buckytubes. Fullerenes are similar in structure to graphite, which is composed of stacked graphene sheets of linked hexagonal rings; but they may also contain pentagonal (or sometimes heptagonal) rings.

In some embodiments, the target object is a polymer and the spatial coordinates are a set of three-dimensional coordinates $\{x1, \ldots, xN\}$ for a crystal structure of the polymer resolved at a resolution of 2.5 Å or better (208). In some embodiments, the target object is a polymer and the spatial coordinates are a set of three-dimensional coordinates $\{x1, \ldots, xN\}$ for a crystal structure of the polymer resolved at a resolution of 3.3 Å or better (210). In some embodiments, the target object is a polymer and the spatial coordinates are a set of three-dimensional coordinates $\{x1, \ldots, xN\}$ for a crystal structure of the polymer resolved (e.g., by X-ray crystallographic techniques) at a resolution of 3.3 Å or better, 3.2 Å or better, 3.1 Å or better, 3.0 Å or better, 2.5 Å or better, 2.2 Å or better, 2.0 Å or better, 1.9 Å or better, 1.85 Å or better, 1.80 Å or better, 1.75 Å or better, or 1.70 Å or better.

In some embodiments, the target object 58 is a polymer and the spatial coordinates are an ensemble of ten or more, twenty or more or thirty or more three-dimensional coordinates for the polymer determined by nuclear magnetic resonance where the ensemble has a backbone RMSD of 1.0 Å or better, 0.9 Å or better, 0.8 Å or better, 0.7 Å or better, 0.6 Å or better, 0.5 Å or better, 0.4 Å or better, 0.3 Å or better, or 0.2 Å or better. In some embodiments the spatial coordinates are determined by neutron diffraction or cryo-electron microscopy (212).

In some embodiments, the target object 58 includes two different types of polymers, such as a nucleic acid bound to a polypeptide. In some embodiments, the native polymer includes two polypeptides bound to each other. In some embodiments, the native polymer under study includes one or more metal ions (e.g. a metalloproteinase with one or more zinc atoms). In such instances, the metal ions and or the organic small molecules may be included in the spatial coordinates 60 for the target object 58.

In some embodiments the target object is a polymer and there are ten or more, twenty or more, thirty or more, fifty or more, one hundred or more, between one hundred and one thousand, or less than 500 residues in the polymer.

In some embodiments, the spatial coordinates of the target object 58 are determined using modeling methods such as ab initio methods, density functional methods, semi-empirical and empirical methods, molecular mechanics, chemical dynamics, or molecular dynamics.

In an embodiment, the spatial coordinates are represented by the Cartesian coordinates of the centers of the atoms comprising the target object. In some alternative embodiments, the spatial coordinates 60 for a target object 58 are represented by the electron density of the target object as measured, for example, by X-ray crystallography. For example, in some embodiments, the spatial coordinates 60 comprise a $2F_{observed}-F_{calculated}$ electron density map computed using the calculated atomic coordinates of the target object 58, where $F_{observed}$ is the observed structure factor amplitudes of the target object and Fc is the structure factor amplitudes calculated from the calculated atomic coordinates of the target object 58.

Thus spatial coordinates 60 for the target object may be received as input data from a variety of sources, such as, but not limited to, structure ensembles generated by solution NMR, co-complexes as interpreted from X-ray crystallography, neutron diffraction, or cryo-electron microscopy, sampling from computational simulations, homology modeling or rotamer library sampling, and combinations of these techniques.

Model a Test Object with the Target Object (214).

In step 214, the test object 72 (or training object) is modeled with the target object 58 in each a plurality of different poses. Here, representative test objects 72 (and training objects 66) in accordance with the present disclosure are first described. Then, modeling and representative modeling techniques are described.

Representative Test Objects 72 (and Training Objects 66).

The significant difference between test objects 72 and training objects 66 is that the training objects 66 are labeled (e.g., with complementary binding data obtained from wet lab binding assays, etc.) and such labeling is used to train the convolutional neural network, whereas the test objects 72 are not labeled and the convolutional neural network is used to classify test objects 72. In other words, the training objects are already classified by labels, and such classification is used to train the convolutional neural network so that the convolutional neural network may then classify the test objects. The test objects are typically not classified prior to application of the convolutional neural network. In typical embodiments, the classifications associated with the training objects 66 is binding data against each of the target objects 58 obtained by wet lab binding assays. As such, in some embodiments, each training object 58 is potentially labeled against several different target objects 58. For instance, consider the case where there are two target objects 58, a first enzyme A (for which inhibitors are sought) and a second enzyme B (for which inhibitors are not sought and for which it is not desirable to inhibit in order to minimize harmful side effects). Each training object 58 will receive a first label against enzyme A and a second label against enzyme B. These first and second labels may be the same or different, for instance they will be different if the training object 58 is a better inhibitor of enzyme A than it is of enzyme B.

In some embodiments, test objects 72 and training objects 66 are organic compounds that satisfy two or more rules, three or more rules, or all four rules of the Lipinski's Rule of Five: (i) not more than five hydrogen bond donors (e.g., OH and NH groups), (ii) not more than ten hydrogen bond acceptors (e.g. N and O), (iii) a molecular weight under 500 Daltons, and (iv) a Log P under 5. The "Rule of Five" is so called because three of the four criteria involve the number five. See, Lipinski, 1997, Adv. Drug Del. Rev. 23, 3, which is hereby incorporated herein by reference in its entirety.

In some embodiments, a test object 72 or training object 66 satisfies one or more criteria in addition to Lipinski's Rule of Five. For example, in some embodiments, the test object 72 or training object 66 has five or fewer aromatic rings, four or fewer aromatic rings, three or fewer aromatic rings, or two or fewer aromatic rings. In some embodiments, a test object 72 or training object 66 is any organic compound having a molecular weight of less than 2000 Daltons, of less than 4000 Daltons, of less than 6000 Daltons, of less than 8000 Daltons, of less than 10000 Daltons, or less than 20000 Daltons.

However, the systems and methods of the present disclosure have no limitation on the size of the test objects 72 or training objects 66. For instance, in some embodiments, such objects are large polymer, such as antibodies.

Modeling.

Turning to element 214 of FIG. 2A, the test objects 72 and/or training objects 66 are modeled with the target objects 58 in each pose of a plurality of different poses. In some embodiments, the target object 58 is a polymer with an active site, the test object (or training object) is a chemical compound, and the modeling comprises docking the test object into the active site of the polymer (216). In some embodiments, the test object 72 or training object 66 is docked onto the target object 58 a plurality of times to form a plurality of poses. In some embodiments, the test object 72 or training object 66 is docked onto the target object 58 twice, three times, four times, five or more times, ten or more times, fifty or more times, 100 or more times, or a 1000 or more times (218). Each such docking represents a different pose of the test object 72 or training object 66 docked onto the target object 58. In some embodiments, the target object 58 is a polymer with an active site and the test object 72 or training object 66 is docked into the active site in each of plurality of different ways, each such way representing a different pose. It is expected that many of these poses are not correct, meaning that such poses do not represent true interactions between the test object 72 (or training object 66) and the target object 58 that arise in nature. Advantageously, during training with the training objects 66, the convolutional neural network will be able to filter out (downweight) incorrect poses because no consistent patterns will arise between the incorrect poses and the training object labels. Without intending to be limited by any particular theory, it is expected that inter-object (e.g., intermolecular) interactions observed among incorrect poses will cancel each other out like white noise whereas the inter-object interactions formed by correct poses formed by training objects 66 will reinforce each other and thus train the weights of the network over time. Thus, during training mode regarding incorrect poses, the neural net would fail to find patterns which explain the difference between the active training objects 66 and the inactive training objects 66 (e.g., to discriminate between labeling data of the training objects). With respect to incorrect poses, the network would learn the weight of the training objects 66, their size, and similar global summary descriptors, but none of the real intermolecular interactions that are formed between the training objects and the test object in nature. Thus, advantageously, the disclosed systems and methods are not sensitive to incorrect poses, particularly when more than 10 poses per training object 66, more than one hundred poses per training object 66, or more than one thousand poses per training object 66 are taken. Likewise, when test objects 72 are sampled, a plurality of poses are also taken. Thus, even within one test or training object, it is expected that the wrong poses will cancel each other out, and the poses that are close enough to imply something close to the kind of inter-object interactions (e.g., intermolecular bonding) that arises in nature, that such poses would be the ones that contribute to the final signal generated by the plurality of poses for a single test or training object.

In some embodiments, training objects 66 and test objects 72 are docked by either random pose generation techniques, or by biased pose generation. In some embodiments, training objects 66 and/or test objects 72 are docked by Markov chain Monte Carlo sampling. In some embodiments, such sampling allows the full flexibility of training objects and/or test objects in the docking calculations and a scoring function that is the sum of the interaction energy between the training (or test) object and the target object 58 as well as the conformational energy of the training (or test) object. See, for example, Liu and Wang, 1999, "MCDOCK: A Monte Carlo simulation approach to the molecular docking problem," Journal of Computer-Aided Molecular Design 13, 435-451, which is hereby incorporated by reference.

In some embodiments, algorithms such as DOCK (Shoichet, Bodian, and Kuntz, 1992, "Molecular docking using shape descriptors," Journal of Computational Chemistry 13(3), pp. 380-397; and Knegtel, Kuntz, and Oshiro, 1997 "Molecular docking to ensembles of protein structures," Journal of Molecular Biology 266, pp. 424-440, each of which is hereby incorporated by reference) are used to find a plurality of poses for each of the test objects 72 and/or training objects 66 against each of the target objects 58. Such algorithms model the target object and the test (or training) object as rigid bodies. The docked conformation is searched using surface complementary to find poses.

In some embodiments, algorithms such as AutoDOCK (Morris et al., 2009, "AutoDock4 and AutoDockTools4: Automated Docking with Selective Receptor Flexibility," J. Comput. Chem. 30(16), pp. 2785-2791; Sotriffer et al., 2000, "Automated docking of ligands to antibodies: methods and applications," Methods: A Companion to Methods in Enzymology 20, pp. 280-291; and "Morris et al., 1998, "Automated Docking Using a Lamarckian Genetic Algorithm and Empirical Binding Free Energy Function," Journal of Computational Chemistry 19: pp. 1639-1662, each of which is hereby incorporated by reference) are used to find a plurality of poses for each of the test objects 72 and/or training objects 66 against each of the target objects 58. AutoDOCK uses a kinematic model of the ligand and supports Monte Carlo, simulated annealing, the Lamarckian Genetic Algorithm, and Genetic algorithms. Accordingly, in some embodiments the plurality of different poses (for a given test object—target object pair or a given training object—test object pair) are obtained by Markov chain Monte Carlo sampling, simulated annealing, Lamarckian Genetic Algorithms, or genetic algorithms, using a docking scoring function (220).

In some embodiments, algorithms such as FlexX (Rarey et al., 1996, "A Fast Flexible Docking Method Using an Incremental Construction Algorithm," Journal of Molecular Biology 261, pp. 470-489, which is hereby incorporated by reference) are used to find a plurality of poses for each of the test objects 72 and/or training objects 66 against each of the target objects 58. FlexX does an incremental construction of the test object 72 and/or training object 66 at the active site of a target object 58 using a greedy algorithm. Accordingly, in some embodiments the plurality of different poses (for a given test object—target object pair or a given training object—test object pair) are obtained by a greedy algorithm (222).

In some embodiments, algorithms such as GOLD (Jones et al., 1997, "Development and Validation of a Genetic Algorithm for flexible Docking," Journal Molecular Biology 267, pp. 727-748, which is hereby incorporated by reference) are used to find a plurality of poses for each of the test objects 72 and/or training objects 66 against each of the target objects 58. GOLD stands for Genetic Optimization for Ligand Docking. GOLD builds a genetically optimized hydrogen bonding network between the test object 72 and/or training object 66 and the target object 58.

In some embodiments, the modeling comprises performing a molecular dynamics run of the target object and the test object. During the molecular dynamics run, the atoms of the target object and the test object are allowed to interact for a fixed period of time, giving a view of the dynamical evolution of the system. The trajectory of atoms in the target object and the test object (or training object) are determined by numerically solving Newton's equations of motion for a system of interacting particles, where forces between the particles and their potential energies are calculated using interatomic potentials or molecular mechanics force fields. See Alder and Wainwright, 1959, "Studies in Molecular Dynamics. I. General Method,". J. Chem. Phys. 31 (2): 459; and Bibcode, 1959, J. Ch. Ph. 31, 459A, doi:10.1063/1.1730376, each of which is hereby incorporated by reference. Thus, in this way, the molecular dynamics run produces a trajectory of the target object and the test object together over time. This trajectory comprises the trajectory of the atoms in the target object and the test object. In some embodiments, a subset of the plurality of different poses is obtained by taking snapshots of this trajectory over a period of time. In some embodiments, poses are obtained from snapshots of several different trajectories, where each trajectory comprise a different molecular dynamics run of the target object interacting with the test object. In some embodiments, prior to a molecular dynamics run, a test object (or a training object) is first docketed into an active site of the target object using a docking technique.

Regardless of what modeling method is used, what is achieved for any given test object 72/training object 66—target object 58 pair is a diverse set of poses of the test/training object with the target object with the expectation that one or more of the poses is close enough to the naturally occurring pose to demonstrate some of the relevant intermolecular interactions between the given test object 72/training object 66—target object 58 pair.

Figure 3:
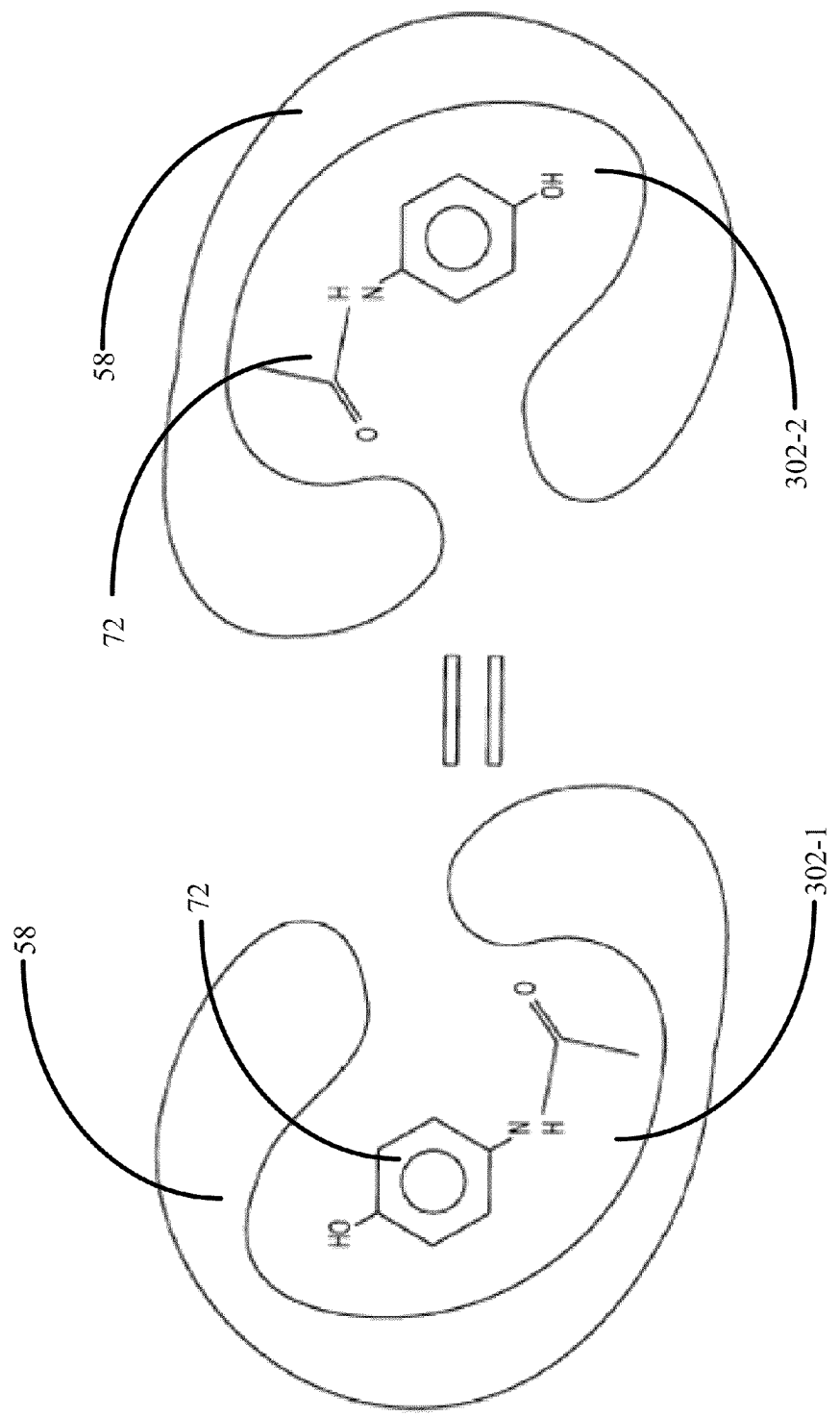
FIG. 3 is a schematic view of an example test object in two different poses relative to a target object, according to an embodiment.

In some embodiments an initial pose of the test object or training object in the active site of a target object 58 is generated using any of the above-described techniques and additional poses are generated through the application of some combination of rotation, translation, and mirroring operators in any combination of the three X, Y and Z planes. Rotation and translation of the test or training object may be randomly selected (within some range, e.g. plus or minus 5 Å from the origin) or uniformly generated at some pre-specified increment (e.g., all 5 degree increments around the circle). FIG. 3 provides a sample illustration of a test object 72 in two different poses 302 in the active site of a target object 58.

Creating a Voxel Map.

Figure 2B:
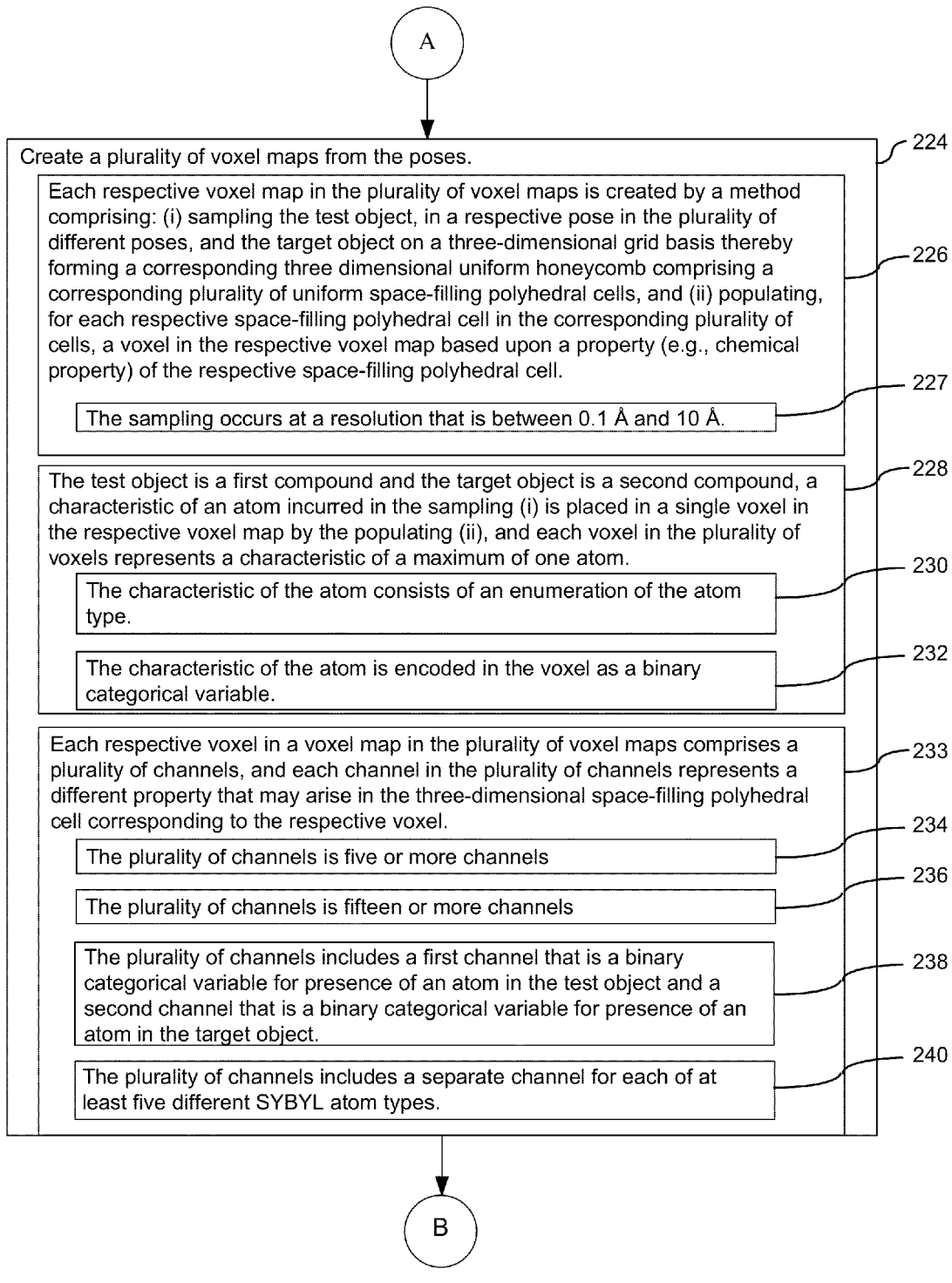
Figure 2C:
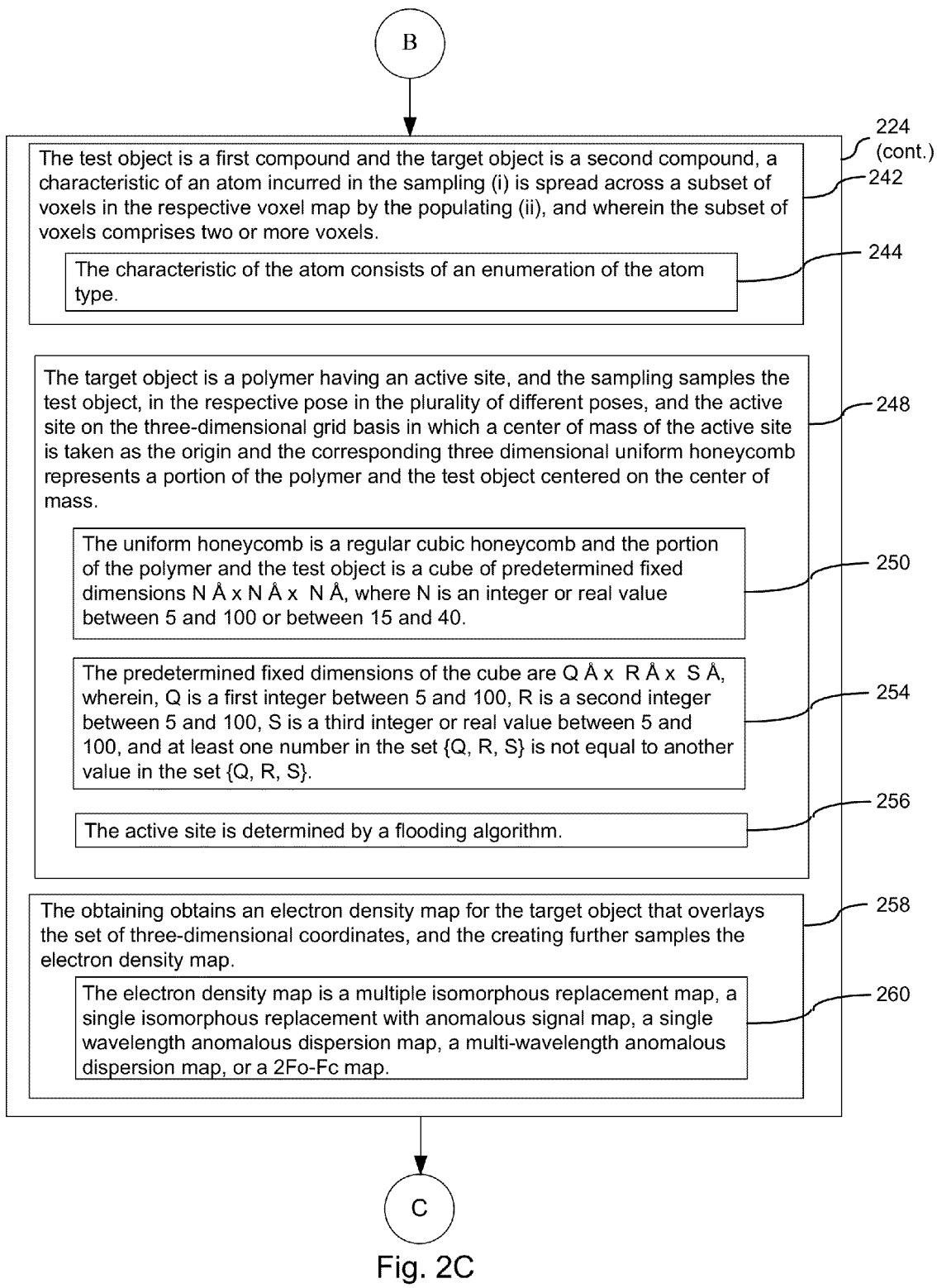
Figure 2D:
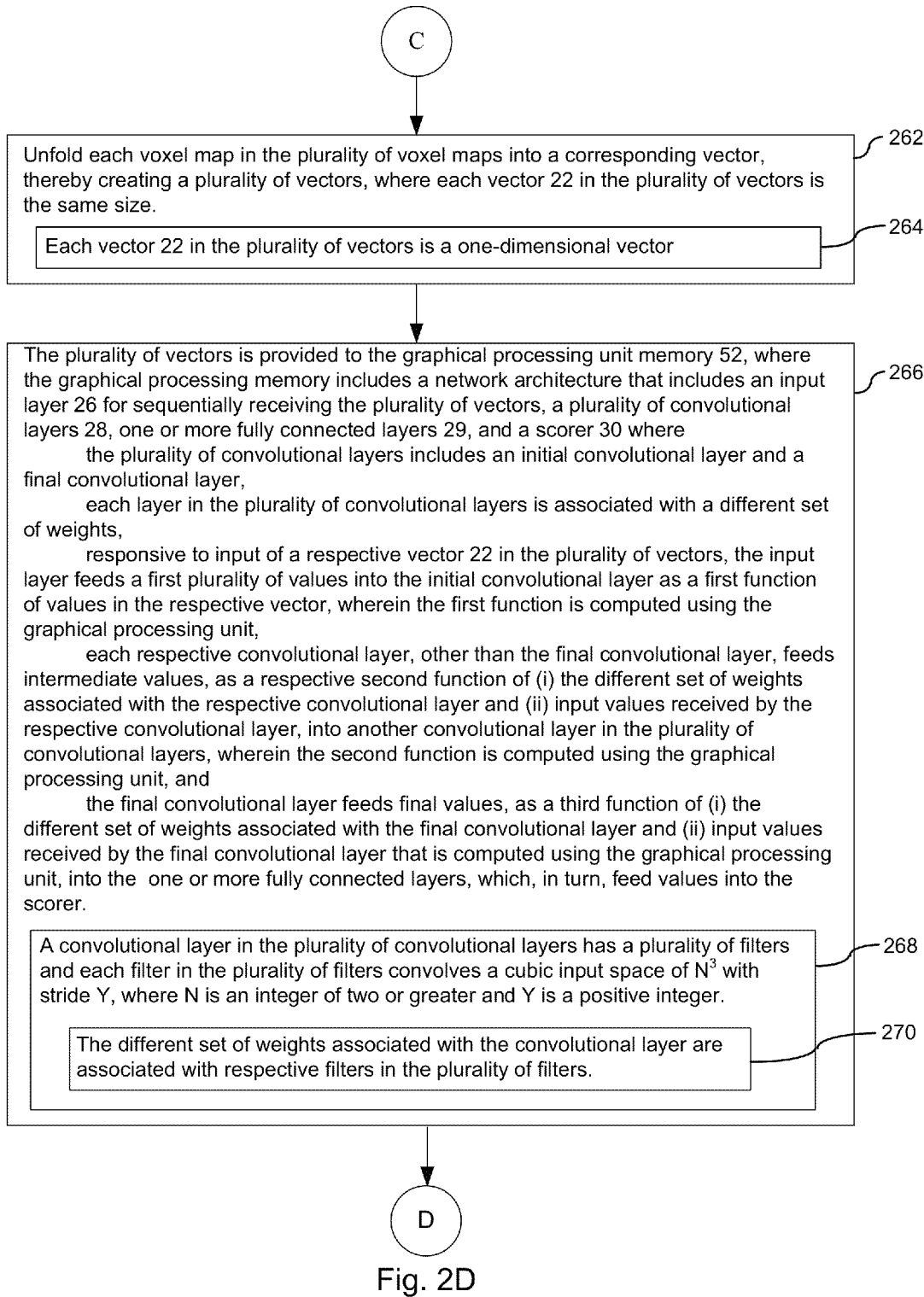

Referring to element 224 of FIG. 2B, after generation of each of the poses for each of the target and/or test objects, a voxel map 40 is created of each pose. In some embodiments, each respective voxel map 40 in the plurality of voxel maps is created by a method comprising: (i) sampling the test object 72 (or training object 68), in a respective pose in the plurality of different poses, and the target object 58 on a three-dimensional grid basis thereby forming a corresponding three dimensional uniform space-filling honeycomb comprising a corresponding plurality of space filling (three-dimensional) polyhedral cells and (ii) populating, for each respective three-dimensional polyhedral cell in the corresponding plurality of three-dimensional cells, a voxel (discrete set of regularly-spaced polyhedral cells) in the respective voxel map 40 based upon a property (e.g., chemical property) of the respective three-dimensional polyhedral cell (226). Thus, if a particular test object has ten poses relative to a target object, ten corresponding voxel maps are created, if a particular test object has one hundred poses relative to a target object, one hundred corresponding voxel maps are created, and so forth. Examples of space filling honeycombs include cubic honeycombs with parallelepiped cells, hexagonal prismatic honeycombs with hexagonal prism cells, rhombic dodecahedra with rhombic dodecahedron cells, elongated dodecahedra with elongated dodecahedron cells, and truncated octahedra with truncated octahedron cells.

In some embodiments, the space filling honeycomb is a cubic honeycomb with cubic cells and the dimensions of such voxels determine their resolution. For example, a resolution of 1 Å may be chosen meaning that each voxel, in such embodiments, represents a corresponding cube of the geometric data with 1 Å dimensions (e.g., 1 Å×1 Å×1 Å in the respective height, width, and depth of the respective cells). However, in some embodiments, finer grid spacing (e.g., 0.1 Å or even 0.01 Å) or coarser grid spacing (e.g. 4 Å) is used, where the spacing yields an integer number of voxels to cover the input geometric data. In some embodiments, the sampling occurs at a resolution that is between 0.1 Å and 10 Å (227). As an illustration, for a 40 Å input cube, with a 1 Å resolution, such an arrangement would yield 40*40*40=64,000 input voxels.

In some embodiments, the test object 72 (or training object 66) is a first compound and the target object 58 is a second compound, a characteristic of an atom incurred in the sampling (i) is placed in a single voxel in the respective voxel map by the populating (ii), and each voxel in the plurality of voxels represents a characteristic of a maximum of one atom (228). In some embodiments, the characteristic of the atom consists of an enumeration of the atom type (230). As one example, for biological data, some embodiments of the disclosed systems and methods are configured to represent the presence of every atom in a given voxel of the voxel map 40 as a different number for that entry, e.g., if a carbon is in a voxel, a value of 6 is assigned to that voxel because the atomic number of carbon is 6. However, such an encoding could imply that atoms with close atomic numbers will behave similarly, which may not be particularly useful depending on the application. Further, element behavior may be more similar within groups (columns on the periodic table), and therefore such an encoding poses additional work for the convolutional neural network 24 to decode.

In some embodiments, the characteristic of the atom is encoded in the voxel as a binary categorical variable (232). In such embodiments, atom types are encoded in what is termed a "one-hot" encoding: every atom type has a separate channel. Thus, in such embodiments, each voxel has a plurality of channels and at least a subset of the plurality of channels represent atom types. For example, one channel within each voxel may represent carbon whereas another channel within each voxel may represent oxygen. When a given atom type is found in the three-dimensional grid element corresponding to a given voxel, the channel for that atom type within the given voxel is assigned a first value of the binary categorical variable, such as "1", and when the atom type is not found in the three-dimensional grid element corresponding to the given voxel, the channel for that atom type is assigned a second value of the binary categorical variable, such as "0" within the given voxel.

While there are over 100 elements, most are not encountered in biology. However, even representing the most common biological elements (i.e., H, C, N, O, F, P, S, Cl, Br, I, Li, Na, Mg, K, Ca, Mn, Fe, Co, Zn) may yield 18 channels per voxel or 10,483*18=188,694 inputs to the receptor field. As such, in some embodiments, each respective voxel in a voxel map 40 in the plurality of voxel maps comprises a plurality of channels, and each channel in the plurality of channels represents a different property that may arise in the three-dimensional space filling polyhedral cell corresponding to the respective voxel (233). The number of possible channels for a given voxel is even higher in those embodiments where additional characteristics of the atoms (for example, partial charge, presence in ligand versus protein target, electronegativity, or SYBYL atom type) are additionally presented as independent channels for each voxel, necessitating more input channels to differentiate between otherwise-equivalent atoms.

In some embodiments, each voxel has five or more input channels (234). In some embodiments, each voxel has fifteen or more input channels (236). In some embodiments, each voxel has twenty or more input channels, twenty-five or more input channels, thirty or more input channels, fifty or more input channels, or one hundred or more input channels. In some embodiments, each voxel has five or more input channels selected from the descriptors found in Table 1 below (240). For example, in some embodiments, each voxel has five or more channels, each encoded as a binary categorical variable where each such channel represents a SYBYL atom type selected from Table 1 below. For instance, in some embodiments, each respective voxel in a voxel map 40 includes a channel for the C.3 (sp3 carbon) atom type meaning that if the grid in space for a given test object—target object (or training object—target object) complex represented by the respective voxel encompasses an sp3 carbon, the channel adopts a first value (e.g., "1") and is a second value (e.g. "0") otherwise.

TABLE 1

| SYBYL Atom Types | |
|---|---|
| SYBYL ATOM TYPE | DESCRIPTION |
| C.3 | sp3 carbon |
| C.2 | sp2 carbon |
| C.ar | aromatic carbon |
| C.1 | sp carbon |
| N.3 | sp3 nitrogen |
| N.2 | sp2 nitrogen |
| N.1 | sp nitrogen |

TABLE 1-continued

| SYBYL Atom Types | |
|---|---|
| SYBYL ATOM TYPE | DESCRIPTION |
| O.3 | sp3 oxygen |
| O.2 | sp2 oxygen |
| S.3 | sp3 sulfur |
| N.ar | aromatic nitrogen |
| P.3 | sp3 phosphorous |
| H | hydrogen |
| Br | bromine |
| Cl | chlorine |
| F | fluorine |
| I | iodine |
| S.2 | sp2 sulfur |
| N.pl3 | pl3 trigonal planar nitrogen |
| LP | lone pair |
| Na | sodium |
| K | potassium |
| Ca | calcium |
| Li | lithium |
| Al aluminum | aluminum |
| Si | silicon |
| N.am | amide nitrogen |
| S.o | sulfoxide sulfur |
| S.o2 | sulfone sulfur |
| N.4 | positively charged nitrogen |
| O.co2 | oxygen in carboxylate or phosphate group |
| C.cat | carbocation, used only in a guadinium group |
| H.spc | hydrogen in SPC water model |
| O.spc | oxygen in SPC water model |
| H.t3p | hydrogen in TIP3P water model |
| O.t3p | oxygen in TIP3P water model |
| ANY | any atom |
| HEV | heavy (non H) atom |
| HET | heteroatom (N, O, S, P) |
| HAL | halogen |
| Mg | magnesium |
| Cr.oh | hydroxy chromium |
| Cr.th | chromium |
| Se | selenium |
| Fe | iron |
| Cu | copper |
| Zn | zinc |
| Sn | tin |
| Mo | molybdenum |
| Mn | manganese |
| Co.oh | hydroxy cobalt |

In some embodiments, each voxel comprises ten or more input channels, fifteen or more input channels, or twenty or more input channels selected from the descriptors found in Table 1 above. In some embodiments, each voxel includes a channel for halogens.

In some embodiments, a structural protein-ligand interaction fingerprint (SPLIF) score is generated for each pose of a given test object (or training object) to a target object and this SPLIF score is used as additional input into the underlying neural network or is individually encoded in the voxel map. For a description of SPLIFs, see Da and Kireev, 2014, J. Chem. Inf. Model. 54, pp. 2555-2561, "Structural Protein—Ligand Interaction Fingerprints (SPLIF) for Structure-Based Virtual Screening: Method and Benchmark Study," which is hereby incorporated by reference. A SPLIF implicitly encodes all possible interaction types that may occur between interacting fragments of the test (or training) object and the target object (e.g., π-π, CH-π, etc.). In the first step, a test (or training) object—target object complex (pose) is inspected for intermolecular contacts. Two atoms are deemed to be in a contact if the distance between them is within a specified threshold (e.g., within 4.5 Å). For each such intermolecular atom pair, the respective test (or training) atom and target object atoms are expanded to circular fragments, e.g., fragments that include the atoms in question and their successive neighborhoods up to a certain distance. Each type of circular fragment is assigned an identifier. In some embodiments, such identifiers are coded in individual channels in the respective voxels. In some embodiments, the Extended Connectivity Fingerprints up to the first closest neighbor (ECFP2) as defined in the Pipeline Pilot software can be used. See, Pipeline Pilot, ver. 8.5, Accelrys Software Inc., 2009, which is hereby incorporated by reference. ECFP retains information about all atom/bond types and uses one unique integer identifier to represent one substructure (i.e., circular fragment). The SPLIF fingerprint encodes all the circular fragment identifiers found. In some embodiments, the SPLIF fingerprint is not encoded individual voxels but serves as a separate independent input in the convolutional neural network 24 discussed below.

In some embodiments, rather than or in addition to SPLIFs, structural interaction fingerprints (SIFt) are computed for each pose of a given test object (or training object) to a target object and independently provided as input into the convolutional neural network 24 discussed below or are encoded in the voxel map. For a computation of Sifts, see Deng et al., 2003, "Structural Interaction Fingerprint (SIFt): A Novel Method for Analyzing Three-Dimensional Protein-Ligand Binding Interactions," J. Med. Chem. 47 (2), pp. 337-344, which is hereby incorporated by reference.

In some embodiments, rather than or in addition to SPLIFs and SIFTs, atom-pairs-based interaction fragments (APIFs) are computed for each pose of a given test object (or training object) to a target object and independently provided as input into the convolutional neural network 24 discussed below or is individually encoded in the voxel map. For a computation of APIFs, see Perez-Nueno et al., 2009, "APIF: a new interaction fingerprint based on atom pairs and its application to virtual screening," J. Chem. Inf. Model. 49(5), pp. 1245-1260, which is hereby incorporated by reference.

Figure 4:
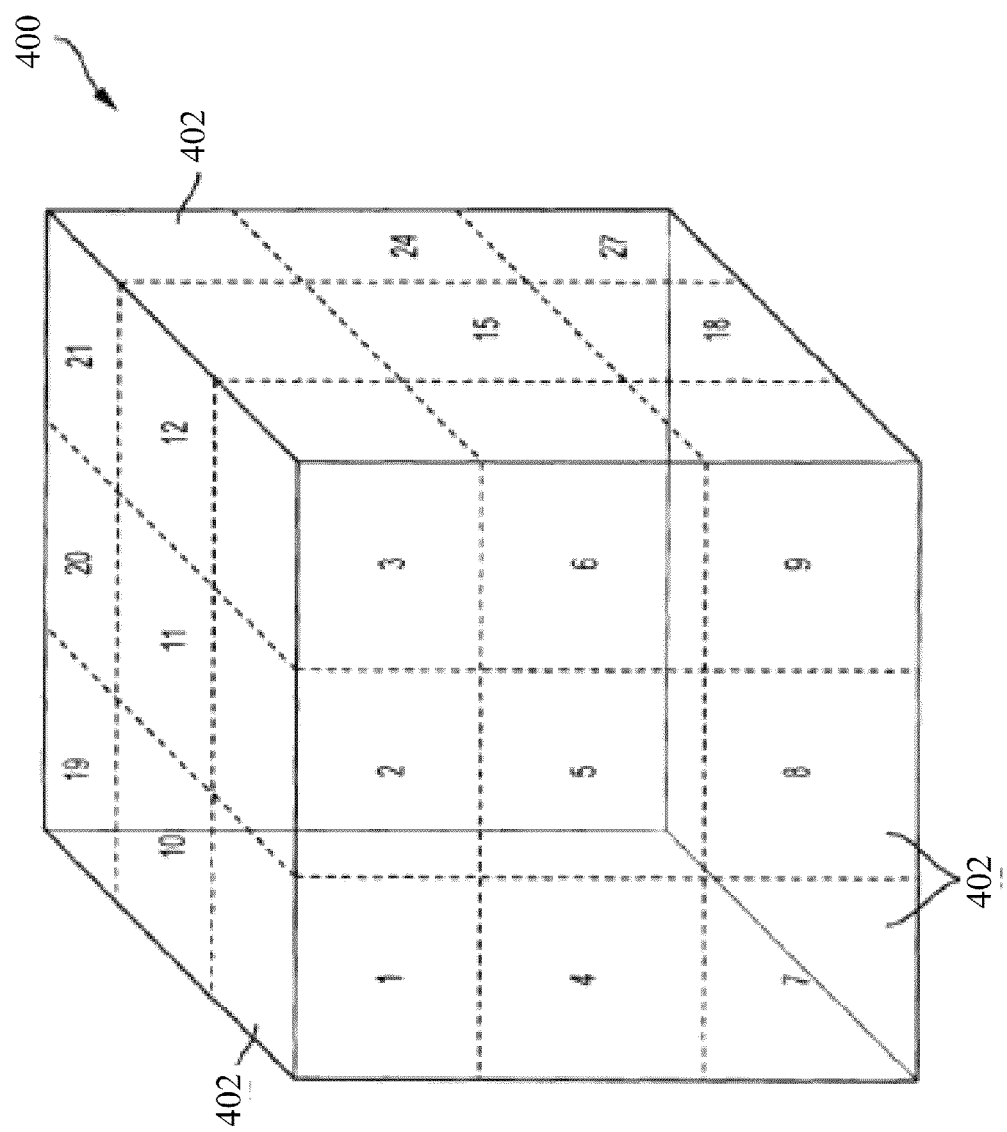
FIG. 4 is a schematic view of a geometric representation of input features in the form of a three-dimensional grid of voxels, according to an embodiment.

The data representation may be encoded with the biological data in a way that enables the expression of various structural relationships associated with molecules/proteins for example. The geometric representation may be implemented in a variety of ways and topographies, according to various embodiments. The geometric representation is used for the visualization and analysis of data. For example, in an embodiment, geometries may be represented using voxels laid out on various topographies, such as 2-D, 3-D Cartesian/Euclidean space, 3-D non-Euclidean space, manifolds, etc. For example, FIG. 4 illustrates a sample three-dimensional grid structure 400 including a series of sub-containers, according to an embodiment. Each sub-container 402 may correspond to a voxel. A coordinate system may be defined for the grid, such that each sub-container has an identifier. In some embodiments of the disclosed systems and methods, the coordinate system is a Cartesian system in 3-D space, but in other embodiments of the system, the coordinate system may be any other type of coordinate system, such as a oblate spheroid, cylindrical or spherical coordinate systems, polar coordinates systems, other coordinate systems designed for various manifolds and vector spaces, among others. In some embodiments, the voxels may have particular values associated to them, which may, for example, be represented by applying labels, and/or determining their positioning, among others.

Because neural networks require a fixed input size, some embodiments of the disclosed systems and methods crop the geometric data (the target-test or target-training object complex) to fit within an appropriate bounding box. For example, a cube of 25-40 Å to a side, may be used. In some embodiments in which the target and/or test objects have been docketed into the active site of target objects 58, the center of the active site serves as the center of the cube.

While in some embodiments a square cube of fixed dimensions centered on the active site of the target object is used to partition the space into the voxel grid, the disclosed systems are not so limited. In some embodiments, any of a variety of shapes is used to partition the space into the voxel grid. In some embodiments, polyhedra, such as rectangular prisms, polyhedra shapes, etc. are used to partition the space.

In an embodiment, the grid structure may be configured to be similar to an arrangement of voxels. For example, each sub-structure may be associated with a channel for each atom being analyzed. Also, an encoding method may be provided for representing each atom numerically.

In some embodiments, the voxel map takes into account the factor of time and may thus be in four dimensions (X, Y, Z, and time).

In some embodiments, other implementations such as pixels, points, polygonal shapes, polyhedrals, or any other type of shape in multiple dimensions (e.g. shapes in 3D, 4D, and so on) may be used instead of voxels.

In some embodiments, the geometric data is normalized by choosing the origin of the X, Y and Z coordinates to be the center of mass of a binding site of the target object as determined by a cavity flooding algorithm (256). For representative details of such algorithms, see Ho and Marshall, 1990, "Cavity search: An algorithm for the isolation and display of cavity-like binding regions," Journal of Computer-Aided Molecular Design 4, pp. 337-354; and Hendlich et al., 1997, "Ligsite: automatic and efficient detection of potential small molecule-binding sites in proteins," J. Mol. Graph. Model 15, no. 6, each of which is hereby incorporated by reference. Alternatively, in some embodiments, the origin of the voxel map is centered at the center of mass of the entire co-complex (of the test object bound to the target object or training object bound to the target object, of just the target object, or of just the test object or training object). The basis vectors may optionally be chosen to be the principal moments of inertia of the entire co-complex, of just the target, or of just the test object/training object. In some embodiments, the target object 58 is a polymer having an active site, and the sampling samples the test object 72 (or training object 66), in each of the respective poses in the plurality of different poses for the test object 72 (or training object 66), and the active site on the three-dimensional grid basis in which a center of mass of the active site is taken as the origin and the corresponding three dimensional uniform honeycomb for the sampling represents a portion of the polymer and the test object 72 (or training object 66) centered on the center of mass (248). In some embodiments, the uniform honeycomb is a regular cubic honeycomb and the portion of the polymer and the test object is a cube of predetermined fixed dimensions. Use of a cube of predetermined fixed dimensions, in such embodiments, ensures that a relevant portion of the geometric data is used and that each voxel map is the same size. In some embodiments, the predetermined fixed dimensions of the cube are N Å×N Å×N Å, where N is an integer or real value between 5 and 100, an integer between 8 and 50, or an integer between 15 and 40 (250, 252). In some embodiments, the uniform honeycomb is a rectangular prism honeycomb and the portion of the polymer and the test object is a rectangular prism predetermined fixed dimensions Q Å×R Å×S Å, wherein Q is a first integer between 5 and 100, R is a second integer between 5 and 100, S is a third integer or real value between 5 and 100, and at least one number in the set {Q, R, S} is not equal to another value in the set {Q, R, S}.

In an embodiment, every voxel has one or more input channels, which may have various values associated with them, which in a simple implementation could be on/off, and may be configured to encode for a type of atom. Atom types may denote the element of the atom, or atom types may be further refined to distinguish between other atom characteristics. Atoms present may then be encoded in each voxel. Various types of encoding may be utilized using various techniques and/or methodologies. As an example encoding method, the atomic number of the atom may be utilized, yielding one value per voxel ranging from one for hydrogen to 118 for ununoctium (or any other element).

However, as discussed above, other encoding methods may be utilized, such as "one-hot encoding," where every voxel has many parallel input channels, each of which is either on or off and encodes for a type of atom. Atom types may denote the element of the atom, or atom types may be further refined to distinguish between other atom characteristics. For example, SYBYL atom types distinguish single-bonded carbons from double-bonded, triple-bonded, or aromatic carbons. For SYBYL atom types, see Clark et al., 1989, "Validation of the General Purpose Tripos Force Field, 1989, J. Comput. Chem. 10, pp. 982-1012, which is hereby incorporated by reference.

In some embodiments, each voxel further includes one or more channels to distinguish between atoms that are part of the target object 58 or cofactors versus part of the test object 72 or training object 66. For example, in one embodiment, each voxel further includes a first channel for the target object 58 and a second channel for the test object 72 or training object 66 (238). When an atom in the portion of space represented by the voxel is from the target object 58, the first channel is set to a value, such as "1", and is zero otherwise (e.g., because the portion of space represented by the voxel includes no atoms or one or more atoms from the test object 72 or training object 66). Further, when an atom in the portion of space represented by the voxel is from the test object 72 or training object 66, the second channel is set to a value, such as "1", and is zero otherwise (e.g., because the portion of space represented by the voxel includes no atoms or one or more atoms from the target object 58). Likewise, other channels may additionally (or alternatively) specify further information such as partial charge, polarizability, electronegativity, solvent accessible space, and electron density. For example, in some embodiments, an electron density map for the target object overlays the set of three-dimensional coordinates, and the creation of the voxel map further samples the electron density map (258). Examples of suitable electron density maps include, but are not limited to, multiple isomorphous replacement maps, single isomorphous replacement with anomalous signal maps, single wavelength anomalous dispersion maps, multi-wavelength anomalous dispersion maps, and 2Fo-Fc maps (260). See McRee, 1993, *Practical Protein Crystallography*, Academic Press, which is hereby incorporated by reference.

In some embodiments, voxel encoding in accordance with the disclosed systems and methods may include additional optional encoding refinements. The following two are provided as examples.

In a first encoding refinement, the required memory may be reduced by reducing the set of atoms represented by a voxel (e.g., by reducing the number of channels represented by a voxel) on the basis that most elements rarely occur in biological systems. Atoms may be mapped to share the same channel in a voxel, either by combining rare atoms (which may therefore rarely impact the performance of the system) or by combining atoms with similar properties (which therefore could minimize the inaccuracy from the combination).

An encoding refinement is to have voxels represent atom positions by partially activating neighboring voxels. This results in partial activation of neighboring neurons in the subsequent neural network and moves away from one-hot encoding to a "several-warm" encoding. For example, it may be illustrative to consider a chlorine atom, which has a van der Waals diameter of 3.5 Å and therefore a volume of 22.4 Å$^3$ when a 1 Å$^3$ grid is placed, voxels inside the chlorine atom will be completely filled and voxels on the edge of the atom will only be partially filled. Thus, the channel representing chlorine in the partially-filled voxels will be turned on proportionate to the amount such voxels fall inside the chlorine atom. For instance, if fifty percent of the voxel volume falls within the chlorine atom, the channel in the voxel representing chlorine will be activated fifty percent. This may result in a "smoothed" and more accurate representation relative to the discrete one-hot encoding. Thus, in some embodiments, the test object is a first compound and the target object is a second compound, a characteristic of an atom incurred in the sampling is spread across a subset of voxels in the respective voxel map 40 and this subset of voxels comprises two or more voxels, three or more voxels, five or more voxels, ten or more voxels, or twenty-five or more voxels (242). In some embodiments, the characteristic of the atom consists of an enumeration of the atom type (244) (e.g., one of the SYBYL atom types).

Thus, voxelation (rasterization) of the geometric data (the docking of a test or training object onto a target object) that has been encoded is based upon various rules applied to the input data.

Figure 5:
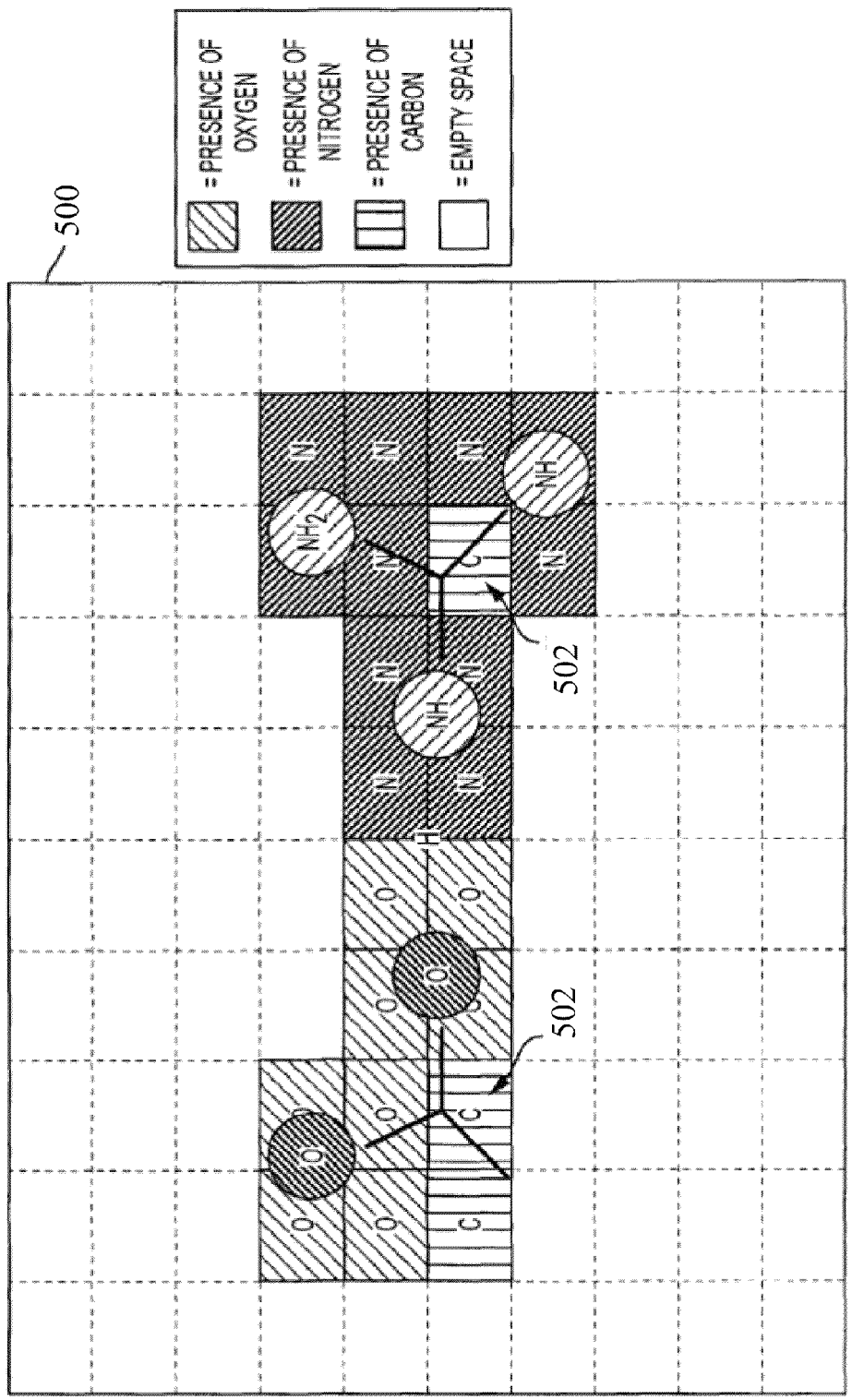
FIG. 5 and FIG. 6 are views of two objects encoded onto a two dimensional grid of voxels, according to an embodiment.
Figure 6:
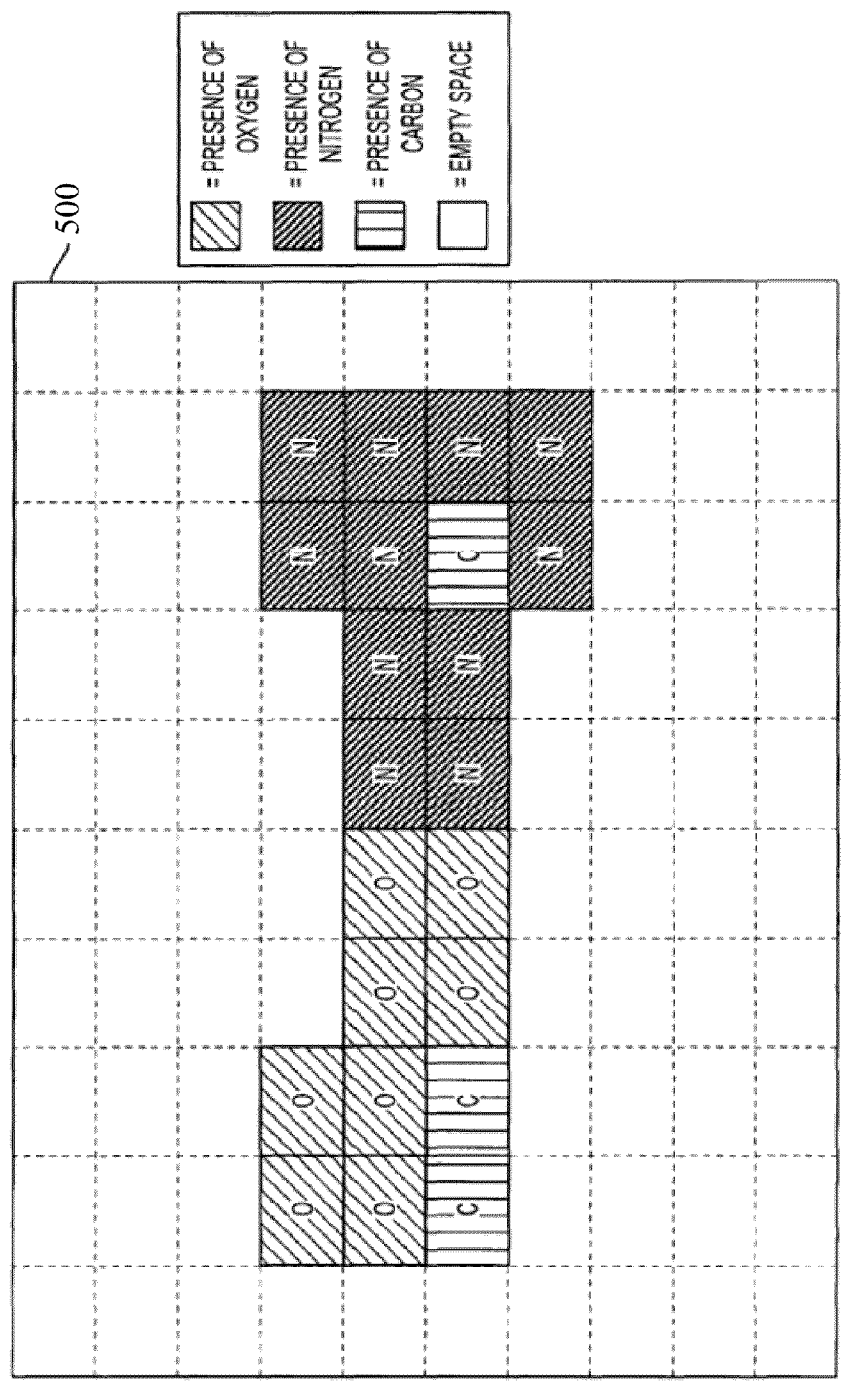
Figure 7:
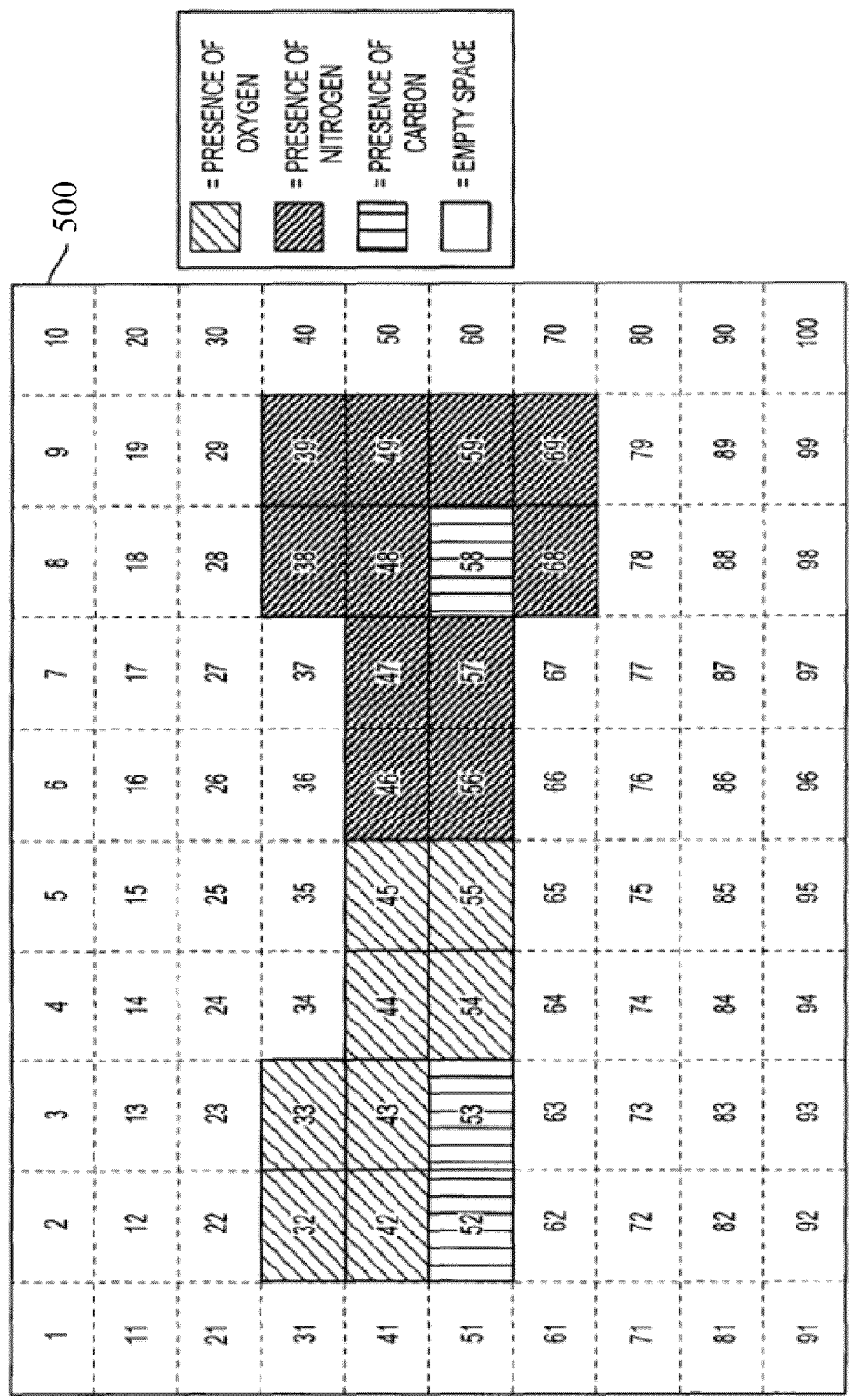
FIG. 7 is the view of the visualization of FIG. 6, in which the voxels have been numbered, according to an embodiment.

FIG. 5 and FIG. 6 provide views of two molecules 502 encoded onto a two dimensional grid 500 of voxels, according to some embodiments. FIG. 5 provides the two molecules superimposed on the two dimensional grid. FIG. 6 provides the one-hot encoding, using the different shading patterns to respectively encode the presence of oxygen, nitrogen, carbon, and empty space. As noted above, such encoding may be referred to as "one-hot" encoding. FIG. 6 shows the grid 500 of FIG. 5 with the molecules 502 omitted. FIG. 7 provides a view of the two dimensional grid of voxels of FIG. 6, where the voxels have been numbered.

Figure 8:
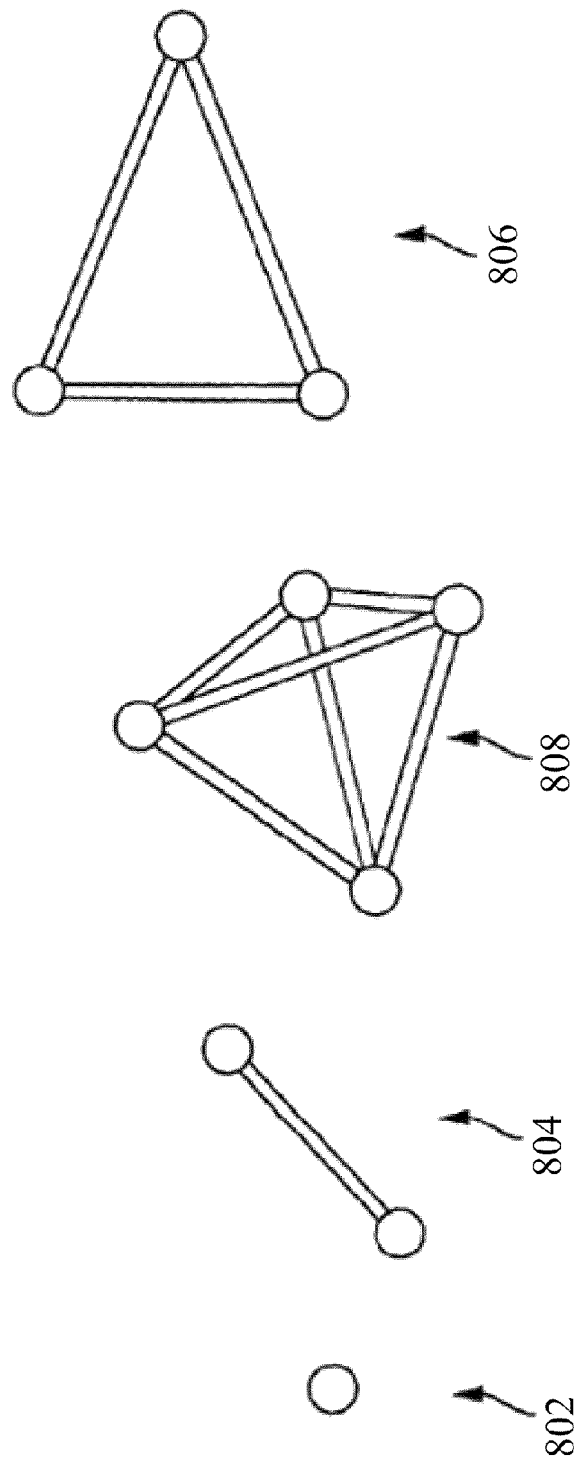
FIG. 8 is a schematic view of geometric representation of input features in the form of coordinate locations of atom centers, according to an embodiment.
Figure 9:
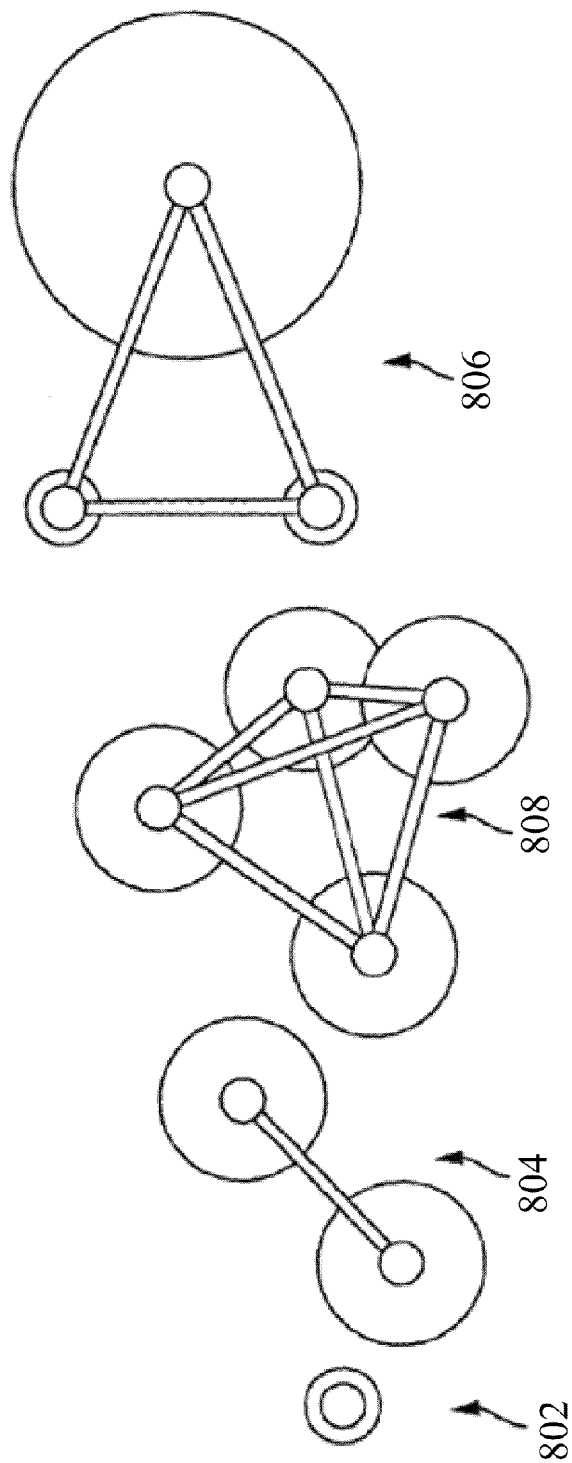
FIG. 9 is schematic view of the coordinate locations of FIG. 8 with a range of locations, according to an embodiment.

In some embodiments, feature geometry is represented in forms other than voxels. FIG. 8 provides view of various representations in which features (e.g., atom centers) are represented as 0-D points (representation 802), 1-D points (representation 804), 2-D points (representation 806), or 3-D points (representation 808). Initially, the spacing between the points may be randomly chosen. However, as the predictive model is trained, the points may be moved closer together, or father apart. FIG. 9 illustrates a range of possible positions for each point.

Unfolding a Voxel Map into a Corresponding Vector.

Referring to element 262, each voxel map 40 is optionally unfolded into a corresponding vector, thereby creating a plurality of vectors, where each vector in the plurality of vectors is the same size. In some embodiments, each vector in the plurality of vectors is a one-dimensional vector (264). For instance, in some embodiments, a cube of 20 Å on each side is centered on the active site of the target object 58 and is sampled with a three-dimensional fixed grid spacing of 1 Å to form corresponding voxels of a voxel map that hold in respective channels basic of the voxel structural features such as atom types as well as, optionally, more complex test object— target object descriptors, as discussed above. In some embodiments, the voxels of this three-dimensional voxel map are unfolded into a one-dimensional floating point vector.

Subjecting a Vector 22 to a Convolutional Neural Network.

Referring to element 266 of FIG. 2, the vectorized representation of voxel maps 22 are subjected to a convolutional network 24. In some embodiments, as illustrated in FIG. 2, the vectorized representation of voxel maps 22 are stored in the memory 52 along with a convolutional assessment module 20, and a convolutional neural network 24. This provides the advantage of processing the vectorized representation of voxel maps 22 through the convolutional neural network 24 at faster speeds. However, in other embodiments, any or all of the vectorized representations of voxel maps 22, the convolutional assessment module 20, and the convolutional neural network 24 are in memory 92 of system 100 or simply are addressable by system 92 across a network. In some embodiments any or all of the vectorized representation of voxel maps 22, the convolutional assessment module 20, and the convolutional neural network 24 are in a cloud computing environment.

In some embodiments, the plurality of vectors 22 is provided to the graphical processing unit memory 52, where the graphical processing unit memory includes a network architecture that includes a convolutional neural network 24 comprising an input layer 26 for sequentially receiving the plurality of vectors, a plurality of convolutional layers 28 and a scorer 30. The plurality of convolutional layers includes an initial convolutional layer and a final convolutional layer. In some embodiments, the convolutional neural network 24 is not in GPU memory but is in the general purpose memory of system 100. In some embodiments, the voxel maps are not vectorized before being input into network 24.

In some embodiments, a convolutional layer 28 in the plurality of convolutional layers comprises a set of learnable filters (also termed kernels). Each filter has fixed three-dimensional size that is convolved (stepped at a predetermined step rate) across the depth, height and width of the input volume of the convolutional layer, computing a dot product (or other functions) between entries (weights) of the filter and the input thereby creating a multi-dimensional activation map of that filter. In some embodiments, the filter step rate is one element, two elements, three elements, four elements, five elements, six elements, seven elements, eight elements, nine elements, ten elements, or more than ten elements of the input space. Thus, consider the case in which a filter has size $5^3$. In some embodiments, this filter will compute the dot product (or other mathematical function) between a contiguous cube of input space that has a depth of five elements, a width of five elements, and a height of five elements, for a total number of values of input space of 125 per voxel channel.

The input space to the initial convolutional layer (e.g., the output from the input layer 26) is formed from either a voxel map 40 or a vectorized representation of the voxel map 22. In some embodiments, the vectorized representation of the voxel map is a one-dimensional vectorized representation of the voxel map which serves as the input space to the initial convolutional layer. Nevertheless, when a filter convolves its input space and the input space is a one-dimensional vectorized representation of the voxel map, the filter still obtains from the one-dimensional vectorized representation those elements that represent a corresponding contiguous cube of fixed space in the target object—test (or training) object complex. In some embodiments, the filter uses standard bookeeping techniques to select those elements from within the one-dimensional vectorized representation that form the corresponding contiguous cube of fixed space in the target object—test (or training) object complex. Thus, in some instances, this necessarily involves taking a non-contiguous subset of element in the one-dimensional vectorized representation in order to obtain the element values of the corresponding contiguous cube of fixed space in the target object—test (or training) object complex.

In some embodiments, the filter is initialized (e.g., to Gaussian noise) or trained to have 125 corresponding weights (per input channel) in which to take the dot product (or some other form of mathematical operation such as the function disclosed in FIG. 14) of the 125 input space values in order to compute a first single value (or set of values) of the activation layer corresponding to the filter. In some embodiment the values computed by the filter are summed, weighted, and/or biased. To compute additional values of the activation layer corresponding to the filter, the filter is then stepped (convolved) in one of the three dimensions of the input volume by the step rate (stride) associated with the filter, at which point the dot product (or some other form of mathematical operation such as the mathematical function disclosed in FIG. 14) between the filter weights and the 125 input space values (per channel) is taken at the new location in the input volume is taken. This stepping (convolving) is repeated until the filter has sampled the entire input space in accordance with the step rate. In some embodiments, the border of the input space is zero padded to control the spatial volume of the output space produced by the convolutional layer. In typical embodiments, each of the filters of the convolutional layer canvas the entire three-dimensional input volume in this manner thereby forming a corresponding activation map. The collection of activation maps from the filters of the convolutional layer collectively form the three-dimensional output volume of one convolutional layer, and thereby serves as the three-dimensional (three spatial dimensions) input of a subsequent convolutional layer. Every entry in the output volume can thus also be interpreted as an output of a single neuron (or a set of neurons) that looks at a small region in the input space to the convolutional layer and shares parameters with neurons in the same activation map. Accordingly, in some embodiments, a convolutional layer in the plurality of convolutional layers has a plurality of filters and each filter in the plurality of filters convolves (in three spatial dimensions) a cubic input space of $N^3$ with stride Y, where N is an integer of two or greater (e.g., 2, 3, 4, 5, 6, 7, 8, 9, 10, or greater than 10) and Y is a positive integer (e.g. 1, 2, 3, 4, 5, 6, 7, 8, 9, 10, or greater than 10) (268).

Each layer in the plurality of convolutional layers is associated with a different set of weights. With more particularity, each layer in the plurality of convolutional layers includes a plurality of filters and each filter comprises an independent plurality of weights (270). In some embodiments, a convolutional layer has 128 filters of dimension $5^3$ and thus the convolutional layer has 128×5×5×5 or 16,000 weights per channel in the voxel map. Thus, if there are five channels in the voxel map, the convolutional layer will have 16,000×5 weights, or 80,000 weights. In some embodiments some or all such weights (and, optionally, biases) of every filter in a given convolutional layer may be tied together, i.e. constrained to be identical.

Responsive to input of a respective vector 22 in the plurality of vectors, the input layer 26 feeds a first plurality of values into the initial convolutional layer as a first function of values in the respective vector, where the first function is optionally computed using the graphical processing unit 50.

Each respective convolutional layer 28, other than the final convolutional layer, feeds intermediate values, as a respective second function of (i) the different set of weights associated with the respective convolutional layer and (ii) input values received by the respective convolutional layer, into another convolutional layer in the plurality of convolutional layers, where the second function is computed using the graphical processing unit 50. For instance, each respective filter of the respective convolutional layer 28 canvasses the input volume (in three spatial dimensions) to the convolutional layer in accordance with the characteristic three-dimensional stride of the convolutional layer and at each respective filter position, takes the dot product (or some other mathematical function) of the filter weights of the respective filter and the values of the input volume (contiguous cube that is a subset of the total input space) at the respect filter position thereby producing a calculated point (or a set of points) on the activation layer corresponding to the respective filter position. The activation layers of the filters of the respective convolutional layer collectively represent the intermediate values of the respective convolutional layer.

The final convolutional layer feeds final values, as a third function of (i) the different set of weights associated with the final convolutional layer and (ii) input values received by the final convolutional layer that is optionally computed using the graphical processing unit 50, into the scorer. For instance, each respective filter of the final convolutional layer 28 canvasses the input volume (in three spatial dimensions) to the final convolutional layer in accordance with the characteristic three-dimensional stride of the convolutional layer and at each respective filter position, takes the dot product (or some other mathematical function) of the filter weights of the filter and the values of the input volume at the respect filter position thereby calculating a point (or a set of points) on the activation layer corresponding to the respective filter position. The activation layers of the filters of the final convolutional layer collectively represent the final values that are fed to scorer 30.

In some embodiments, the convolutional neural network has one or more activation layers. In some embodiments, the activation layer is a layer of neurons that applies the non-saturating activation function $f(x)=\max(0, x)$. It increases the nonlinear properties of the decision function and of the overall network without affecting the receptive fields of the convolution layer. In other embodiments, the activation layer has other functions to increase nonlinearity, for example, the saturating hyperbolic tangent function $f(x)=\tan h$, $f(x)=|\tan h(x)|$, and the sigmoid function $f(x)=(1+e^{-x})^{-1}$. Nonlimiting examples of other activation functions found in other activation layers in some embodiments for the neural network may include, but are not limited to, logistic (or sigmoid), softmax, Gaussian, Boltzmann-weighted averaging, absolute value, linear, rectified linear, bounded rectified linear, soft rectified linear, parameterized rectified linear, average, max, min, some vector norm LP (for $p=1, 2, 3, \ldots, \infty$), sign, square, square root, multiquadric, inverse quadratic, inverse multiquadric, polyharmonic spline, and thin plate spline.

The network 24 learns filters within the convolutional layers 28 that activate when they see some specific type of feature at some spatial position in the input. As discussed in the network training section below, in some embodiments, the initial weights of each filter in a convolutional layer are obtained by training the convolutional neural network against the object training library 64 as discussed below. Accordingly, the operation of the convolutional neural network 24 may yield more complex features than the features historically used to conduct binding affinity prediction. For example, a filter in a given convolutional layer of the network 24 that serves as a hydrogen bond detector may be able to recognize not only that a hydrogen bond donor and acceptor are at a given distance and angles, but also recognize that the biochemical environment around the donor and acceptor strengthens or weakens the bond. Additionally, the filters within the network 24 may be trained to effectively discriminate binders from non-binders in the underlying data.

In some embodiments, the convolutional neural network 24 is configured to adapt for dynamic systems, such as the alternative positions that may be encountered as both the target object and the test object move. In such a target object—test object complex, a number of different configurations may be adopted, with the relative proportion based on the Boltzmann distribution of the free energy of each shape. Both the enthalpic and entropic components of the free energy of the target object—test object complex can depend on the poses adopted by the object ($\Delta G=\Delta H-T \Delta S$). The final binding affinity may be found to be a function of the weighted average of the energies of the set of poses available to the target object—test object complex. To model this physical phenomenon, the convolutional neural network 24 may be configured to sample a large number of alternative positions due to target object and test object motion and to base its binding affinity predictions on this sampled set of configurations of the complex (e.g., by taking the weighted average of all the network 24 scores of these various alternative positions).

As described above, in some embodiments the neural network 24 is configured to develop three-dimensional convolutional layers. The input region to the lowest level convolutional layer 28 may be a cube (or other contiguous region) of voxel channels from the receptive field. Higher convolutional layers 28 evaluate the output from lower convolutional layers, while still having their output be a function of a bounded region of voxels which are close together (in 3-D Euclidean distance).

Biological activity may be invariant under rotation, as well as translation, so the network 24 may be optionally configured to generate rotated feature maps that take advantage of the rotational symmetries of space partitioning. For example, if the system was configured to use cubes to partition the input data, the system could be configured to generate rotated feature maps by tying the weights of the function computations together after a 90 degree rotation.

It may be illustrative to consider a cube which is rotated clockwise: the weights in the upper face of one filter become tied to the weights in the right face of a different filter; in other words, the weights may be constrained to be identical. Rotation may generate 24 feature maps by rotating clockwise by 90 degrees, 180 degrees, 270 degrees, for each of the three XY/XZ/YZ planes. This arrangement reduces the number of parameters to ¹⁄₂₄th of without rotational weight tying, since without weight tying every filter has its own weights.

As an alternative example, if the system were configured to use other polyhedra to partition the input data, the system may be configured to use other rotations to access the isometries appropriate to their symmetry groups. For example, where space has been partitioned using truncated octahedrons, there would be 3 axes of 90 degree rotational symmetry, 4 axes of 120 degree rotational symmetry, and six axes of 180 degree symmetry.

In an embodiment, the network 24 is configured to apply regularization techniques to reduce the tendency of the models to overfit the training objects 66 and training binding data 68.

Zero or more of the network layers in network 24 may consist of pooling layers. As in a convolutional layer, a pooling layer is a set of function computations that apply the same function over different spatially-local patches of input. For pooling layers, the output is given by a pooling operators, e.g. some vector norm LP for p=1, 2, 3, . . . , ∞, over several voxels. Pooling is typically done per channel, rather than across channels. Pooling partitions the input space into a set of three-dimensional boxes and, for each such sub-region, outputs the maximum. The pooling operation provides a form of translation invariance. The function of the pooling layer is to progressively reduce the spatial size of the representation to reduce the amount of parameters and computation in the network, and hence to also control overfitting. In some embodiments a pooling layer is inserted between successive convolutional 28 layers in network 24. Such a pooling layer operates independently on every depth slice of the input and resizes it spatially. In addition to max pooling, the pooling units can also perform other functions, such as average pooling or even L2-norm pooling.

Zero or more of the layers in network 24 may consist of normalization layers, such as local response normalization or local contrast normalization, which may be applied across channels at the same position or for a particular channel across several positions. These normalization layers may encourage variety in the response of several function computations to the same input.

In some embodiments, the scorer 30 comprises a plurality of fully-connected layers and an evaluation layer where a fully-connected layer in the plurality of fully-connected layers feeds into the evaluation layer (272). Neurons in a fully connected layer have full connections to all activations in the previous layer, as seen in regular neural networks. Their activations can hence be computed with a matrix multiplication followed by a bias offset. In some embodiments, each fully connected layer has 512 hidden units, 1024 hidden units, or 2048 hidden units. In some embodiments there are no fully connected layers, one fully connected layer, two fully connected layers, three fully connected layers, four fully connected layers, five fully connected layers, six or more fully connected layers or ten or more fully connected layers in the scorer.

In some embodiments, the evaluation layer discriminates between a plurality of activity classes. In some embodiments, the evaluation layer comprises a logistic regression cost layer over a two activity classes, three activity classes, four activity classes, five activity classes, or six or more activity classes.

In some embodiments, the evaluation layer comprises a logistic regression cost layer over a plurality of activity classes. In some embodiments, the evaluation layer comprises a logistic regression cost layer over a two activity classes, three activity classes, four activity classes, five activity classes, or six or more activity classes.

In some embodiments, the evaluation layer discriminates between two activity classes and the first activity classes (first classification) represents an $IC_{50}$, $EC_{50}$ or KI for the test object (or training object) with respect to the target object that is above a first binding value, and the second activity class (second classification) is an $IC_{50}$, $EC_{50}$, or KI for the test object (or training object) with respect to the target object that is below the first binding value. In some embodiments, the first binding value is one nanomolar, ten nanomolar, one hundred nanomolar, one micromolar, ten micromolar, one hundred micromolar, or one millimolar.

In some embodiments, the evaluation layer comprises a logistic regression cost layer over two activity classes and the first activity classes (first classification) represents an $IC_{50}$, $EC_{50}$ or KI for the test object (or training object) with respect to the target object that is above a first binding value, and the second activity class (second classification) is an $IC_{50}$, $EC_{50}$, or KI for the test object (or training object) with respect to the target object that is below the first binding value. In some embodiments, the first binding value is one nanomolar, ten nanomolar, one hundred nanomolar, one micromolar, ten micromolar, one hundred micromolar, or millimolar.

In some embodiments, the evaluation layer discriminates between three activity classes and the first activity classes (first classification) represents an $IC_{50}$, $EC_{50}$ or KI for the test object (or training object) with respect to the target object that is above a first binding value, the second activity class (second classification) is an $IC_{50}$, $EC_{50}$, or KI for the test object (or training object) with respect to the target object that is between the first binding value and a second binding value, and the third activity class (third classification) is an $IC_{50}$, $EC_{50}$, or KI for the test object (or training object) with respect to the target object that is below the second binding value, where the first binding value is other than the second binding value.

In some embodiments, the evaluation layer comprises a logistic regression cost layer over three activity classes and the first activity classes (first classification) represents an $IC_{50}$, $EC_{50}$ or KI for the test object (or training object) with respect to the target object that is above a first binding value, the second activity class (second classification) is an $IC_{50}$, $EC_{50}$, or KI for the test object (or training object) with respect to the target object that is between the first binding value and a second binding value, and the third activity class (third classification) is an $IC_{50}$, $EC_{50}$, or KI for the test object (or training object) with respect to the target object that is below the second binding value, where the first binding value is other than the second binding value.

In some embodiments, the scorer 30 comprises a fully connected single layer or multilayer perceptron. In some embodiments the scorer comprises a support vector machine, random forest, nearest neighbor. In some embodiments, the scorer 30 assigns a numeric score indicating the strength (or confidence or probability) of classifying the input into the various output categories. In some cases, the categories are binders and nonbinders or, alternatively, the potency level ($IC_{50}$, $EC_{50}$ or KI potencies of e.g., <1 molar, <1 millimolar, <100 micromolar, <10 micromolar, <1 micromolar, <100 nanomolar, <10 nanomolar, <1 nanomolar).

Obtaining a Plurality of Scores from the Scorer (276) and Using a Score from the Convolutional Neural Network to Characterize the Test Object (278).

Figure 2E:
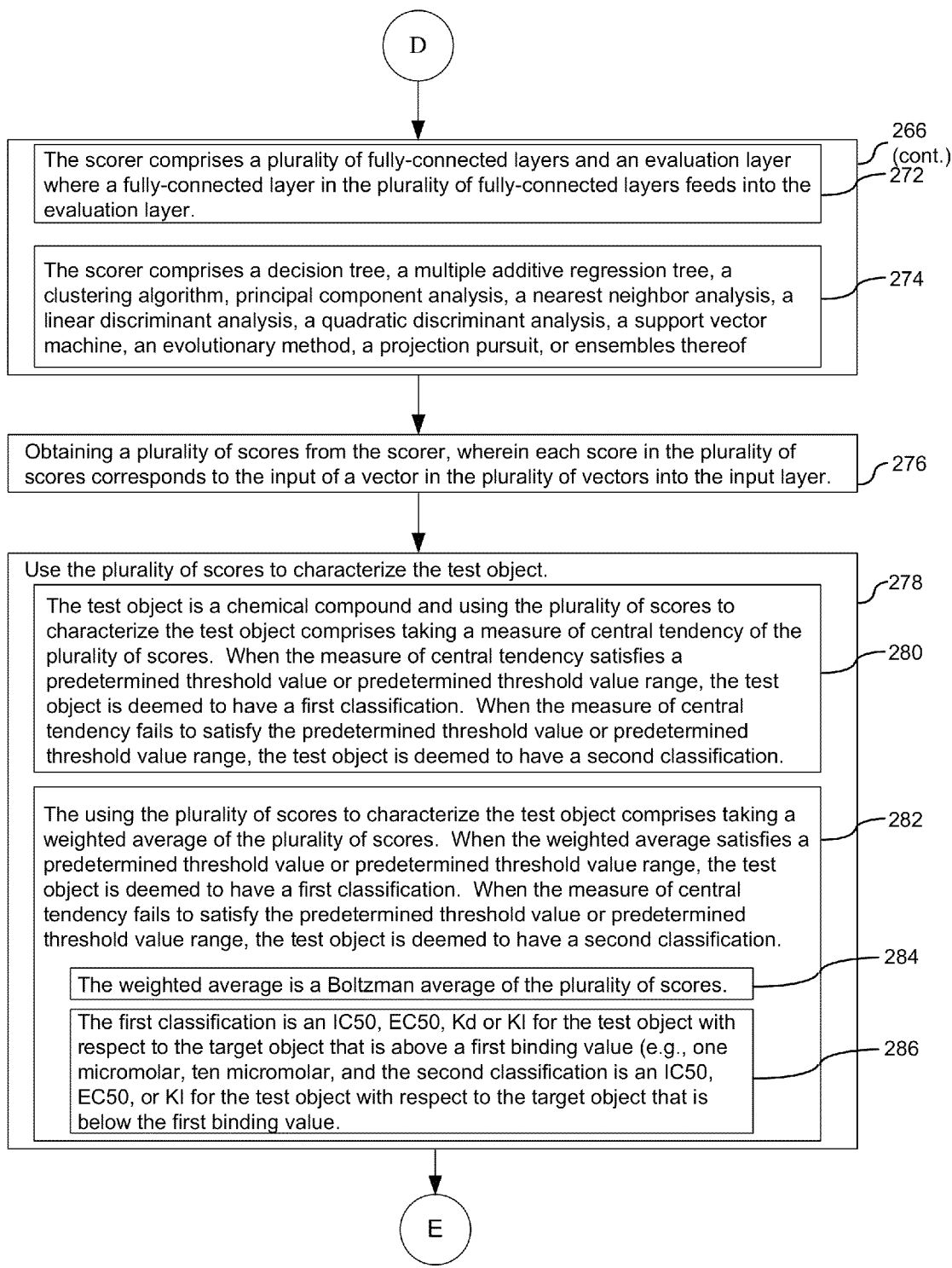
Figure 2F:
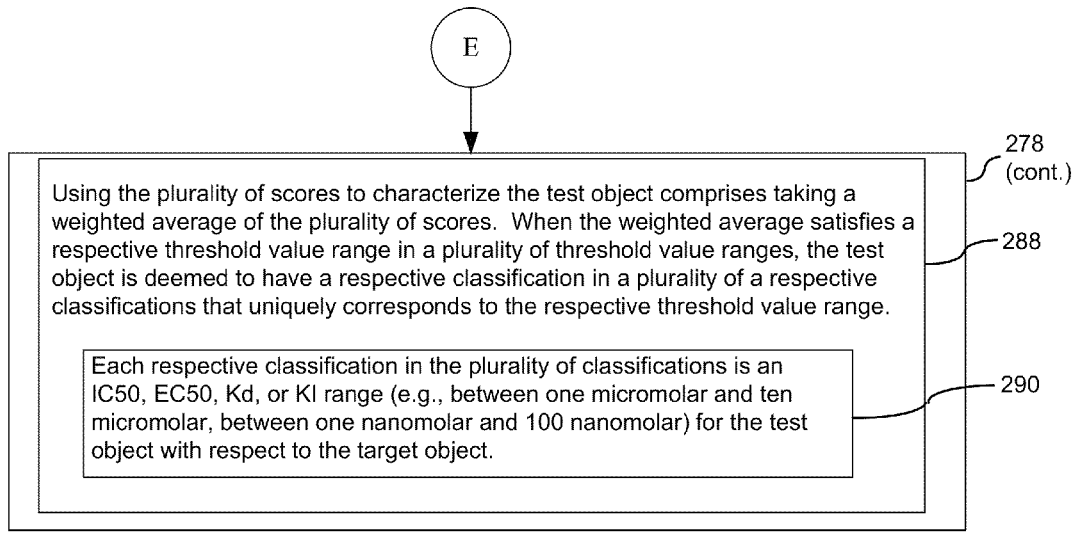

Details for obtaining a scorer score from the neural network 24 for a complex between a test object 72 (or training object 66) and a target object 58 have been described above. As discussed above, each test object 72 (or training object 66) is docked into a plurality of poses with respect to the target object. To present all such poses at once to the convolutional neural network 24 may require a prohibitively large input field (e.g., an input field of size equal to number of voxels*number of channels*number of poses). While in some embodiments all poses are concurrently presented to the network 24, in preferred embodiments each such pose is processed into a voxel map, vectorized, and serves as sequential input into convolutional neural network 24. Referring to FIG. 2E, in this way, a plurality of scores are obtained from the scorer 30, where each score in the plurality of scores corresponds to the input of a vector in the plurality of vectors into the input layer 26 of the scorer 30 (276). In some embodiments, the scores for each of the poses of a given test object 72

(or training object 66) with a given target object 58 are combined together to produce a final score for the entire test object 72 (or training object 66).

In an embodiment where the scorer output is numeric, the outputs may be combined using any of the activation functions described herein are that are known or developed. Examples include, but are not limited to, a non-saturating activation function $f(x)=\max(0, x)$, a saturating hyperbolic tangent function $f(x)=\tan h$, $f(x)=|\tan h(x)|$, the sigmoid function $f(x)=(1+e^{-x})^{-1}$, logistic (or sigmoid), softmax, Gaussian, Boltzmann-weighted averaging, absolute value, linear, rectified linear, bounded rectified linear, soft rectified linear, parameterized rectified linear, average, max, min, some vector norm LP (for $p=1, 2, 3, \ldots, \infty$), sign, square, square root, multiquadric, inverse quadratic, inverse multiquadric, polyharmonic spline, and thin plate spline.

In some embodiments of the present disclosure, the system may be configured to utilize the Boltzmann distribution to combine outputs, as this matches the physical probability of poses if the outputs are interpreted as indicative of binding energies. In other embodiments of the invention, the max( ) function may also provide a reasonable approximation to the Boltzmann and is computationally efficient.

In an embodiment where the scorer output is not numeric, the scorer 30 may be configured to combine the outputs using utilize various ensemble voting schemes, which may include, as illustrative, non limiting examples, majority, weighted averaging, Condorcet methods, Borda count, among others.

In an embodiment, the system may be configured to apply an ensemble of scorerss 30, e.g., to generate indicators of binding affinity.

Referring to element 280 of FIG. 2E, in some embodiments, the test object 72 (or training object 66) is a chemical compound and using the plurality of scores (from the plurality of poses for the test or training object) to characterize (e.g. determine a classification) of the test (or training) object comprises taking a measure of central tendency of the plurality of scores. When the measure of central tendency satisfies a predetermined threshold value or predetermined threshold value range, the test object is deemed to have a first classification. When the measure of central tendency fails to satisfy the predetermined threshold value or predetermined threshold value range, the test object is deemed to have a second classification (280).

Referring to element 282 of FIG. 2E, in some embodiments the using the plurality of scores characterize the test object 72 (or training object 66) comprises taking a weighted average of the plurality of scores (from the plurality of poses for the test or training object). When the weighted average satisfies a predetermined threshold value or predetermined threshold value range, the test object is deemed to have a first classification. When the weighted average fails to satisfy the predetermined threshold value or predetermined threshold value range, the test object is deemed to have a second classification. In some embodiments, the weighted average is a Boltzman average of the plurality of scores (284). In some embodiments, the first classification is an $IC_{50}$, $EC_{50}$ or KI for the test object (or training object) with respect to the target object that is above a first binding value (e.g., one nanomolar, ten nanomolar, one hundred nanomolar, one micromolar, ten micromolar, one hundred micromolar, or one millimolar) and the second classification is an $IC_{50}$, $EC_{50}$, Kd, or KI for the test object with respect to the target object that is below the first binding value (286).

Referring to element 288 of FIG. 2E, in some embodiments the using the plurality of scores to characterize the test object 72 (or training object 66) comprises taking a weighted average of the plurality of scores (from the plurality of poses for the test or training object). When the weighted average satisfies a respective threshold value range in a plurality of threshold value ranges, the test (or training) object is deemed to have a respective classification in a plurality of a respective classifications that uniquely corresponds to the respective threshold value range. In some embodiments, each respective classification in the plurality of classifications is an $IC_{50}$, $EC_{50}$, Kd, or KI range (e.g., between one micromolar and ten micromolar, between one nanomolar and 100 nanomolar) for the test object with respect to the target object (290).

In some embodiments, a single pose for each respective test object against a given target object is run through the neural network 24 and the respective score assigned by the neural network 24 for each of the respective test objects on this basis is used to classify the test objects.

In some embodiments, the weighted mean average of the network 24 scores of one or more poses of a test object against each of a plurality of target objects 58 evaluated by the neural network 24 using the techniques disclosed herein is used to classify the test object. For instance, in some embodiments, the plurality of target objects 58 are taken from a molecular dynamics run in which each target object in the plurality of target objects represents the same polymer at a different time step during the molecular dynamics run. A voxel map of each of one or more poses of the test object against each of these target objects is evaluated against the network 24 to obtain a score for each independent pose—target object pair and the weighted mean average of these scores is used to classify the target object.

Training the Predictive Model.

In some embodiments, where a deep neural network is implemented (e.g., the convolutional neural network 24), the convolutional assessment module 20 is configured to train the network 24 to receive the geometric data input and to output a prediction (probability) of whether or not a given test object binds to a target object. For instance, in some embodiments, the training objects 66, which have known binding data against the target objects (because of their associated binding data 68) are sequentially run through the neural network 24 using the techniques discussed above in relation to FIG. 2 and the neural network provides a single value for each respective training object.

In some such embodiments, the neural network outputs one of two possible activity classes for each training object against a given target object. For instance, the single value provided for each respective training object by the neural network 24 is in a first activity class (e.g., binders) when it is below a predetermined threshold value and is in a second activity class (e.g., nonbinders) when the number is above the predetermined threshold value. The activity classes assigned by the neural network 24 are compared to the actual activity classes as represented by the training object binding data 68. In typical non-limiting embodiments, such training object binding data 68 is from independent web lab binding assays. Errors in activity class assignments made by the neural network, as verified against the binding data 68, are then back-propagated through the weights of the neural network in order to train the neural network 24. For instance, the filter weights of respective filters in the convolutional layers 28 of the network are adjusted in such back-propagation. In an exemplary embodiment, the neural network 24 is trained against the errors in the activity class assignments made by the network 24, in view of the binding data 68, by stochastic gradient descent with the AdaDelta adaptive learning method (Zeiler, 2012 "ADADELTA: an adaptive learning rate method," CoRR, vol. abs/1212.5701, which is hereby incorporated by reference), and the back propagation algorithm provided in Rumelhart et al., 1988, "Neurocomputing: Foundations of research," ch. Learning Representations by Back-propagating Errors, pp. 696-699, Cambridge, Mass., USA: MIT Press, which is hereby incorporated by reference. In some such embodiments the two possible activity classes are respectively a binding constant greater than a given threshold amount (e.g., an $IC_{50}$, $EC_{50}$, or KI for the training object with respect to the target object that is greater than one nanomolar, ten nanomolar, one hundred nanomolar, one micromolar, ten micromolar, one hundred micromolar, or one millimolar) and a binding constant that is below the given threshold amount (e.g., an $IC_{50}$, $EC_{50}$, or KI for the training object with respect to the target object that is less than one nanomolar, ten nanomolar, one hundred nanomolar, one micromolar, ten micromolar, one hundred micromolar, or one millimolar). In some such embodiments, a plurality of poses for each training object against a given target object are sequentially run through the neural network and the weighted average of the scores for these poses as computed by the neural network 24 is compared to binding data 68 that is acquired by wet lab binding assays.

In some such embodiments, the neural network outputs one of a plurality of possible activity classes (e.g., three or more activity classes, four or more activity classes, five or more activity classes) for each training object against a given target object. For instance, the single value provided for each respective training object by the neural network 24 (e.g., the weighted average of a plurality of poses or a single value from a single pose) is in a first activity class when the number falls into a first range, is in a second activity class when the number falls into a second range, is in a third activity class when the number falls into a third range, and so forth. The activity classes assigned by the neural network 24 are compared to the actual activity classes as represented by the training object binding data 68. Errors in activity class assignments made by the neural network, as verified against the binding data 68, are then used to train the neural network 24 using the techniques discussed above. In some embodiments, each respective classification in the plurality of classifications is an $IC_{50}$, $EC_{50}$ or KI range for the training object with respect to the target object.

In some embodiments, a single pose for each respective training object against a given target object is run through the neural network and the resulting respective score assigned by the neural network 24 for each respective training object is compared to binding data 68 for the respective training object that has been separately acquired by one or more wet lab binding assay techniques. Then, errors in activity class assignments made by the neural network 24 for the training objects, as verified against the binding data 68 for the training objects, are used to train the neural network 24 using the techniques discussed above.

In some embodiments, the weighted mean average of one or more poses of a training object against each of a plurality of target objects 58 evaluated by the neural network 24 using the techniques disclosed herein is compared to the binding data 68 for the respective training objects that is separately acquired by one or more wet lab binding assay techniques. For instance, in some embodiments, the plurality of target objects 58 are taken from a molecular dynamics run in which each target object in the plurality of target objects represents the same polymer at a different time step during the molecular dynamics run. Discrepancies between target object classification by the neural network 24 and the object classification by the wet lab binding assays are then used to train the neural network 24 using the techniques discussed above.

In some embodiments, neural network 24 classification of a plurality of training objects is compared to the binding data 68 using non-parametric techniques. For instance, the neural network 24 is used to rank order the plurality of training objects with respect to a given property (e.g., binding against a given target object) and this rank order is compared to the rank order provided by the binding data 68 that is acquired by wet lab binding assays for the plurality of training objects. This gives rise to the ability to train the network 24 on the errors in the calculated rank order using the network 24 error correction techniques discussed above. In some embodiments, the error (differences) between the ranking by the training objects by the neural network 24 and the ranking of the training objects as determined by the binding data 68 is computed using a Wilcoxon Mann Whitney function (Wilcoxon signed-rank test) or other non-parametric test and this error is back-propagated through the neural network 24 in order to further train the network using the neural network 24 error correction techniques discussed above.

In an embodiment where the deep learning techniques utilizes a neural network 24 as described above, the convolutional assessment module 20 may be configured to train the network 24 to improve the accuracy of its prediction by modifying the weights in the filters in the convolutional layers 28 as well as the biases in the network layers. The weights and biases may be further constrained with various forms of regularization such as L1, L2, weight decay, and dropout.

In an embodiment, the neural network 24 may optionally be configured to tune the weights of the network to model the input distribution of the training data through greedy, layer-wise, generative pre-training against the training objects using the contrastive divergence algorithm.

In an embodiment, the neural network 24 may optionally, where training data is labeled (e.g., with the binding data 68), tune the weights within the network 24 to potentially minimize the error between the neural network's predicted binding affinities and/or categorizations and the training data's reported binding affinities and/or categorizations. Various methods may be used to minimize error function, such as gradient descent methods, which may include, but are not limited to, log-loss, sum of squares error, hinge-loss methods. These methods may include second-order methods or approximations such as momentum, Hessian-free estimation, Nesterov's accelerated gradient, adagrad, etc. Unlabelled generative pretraining and labeled discriminative training may also be combined.

Input geometric data may be grouped into training examples. For example, it is often the case that a single set of molecules, cofactors, and protein has multiple geometric measurements, where each "snapshot" describes alternative conformations and poses that the target object and the training objects (or test objects) may adopt. Similarly, in instances where the target object is a protein, different tautomers for the protein sidechains, cofactors, and the training (or test) objects may also be sampled. Because these states all contribute to the behavior of the biological system, as per the Boltzmann distribution, a system to predict binding affinity may be configured to consider these states together (for instance by taking the weighted average of these samplings). Optionally, these training examples may be labeled with binding information. If quantitative binding information is available (e.g., binding data 68), the labels may be the numerical binding affinities. Alternatively, the training examples may be assigned labels from a set of two or more ordered categories (e.g., two categories of binders and nonbinders, or several possibly-overlapping categories describing the ligands as binders of potencies <1 molar, <1 millimolar, <100 micromolar, <10 micromolar, <1 micromolar, <100 nanomolar, <10 nanomolar, <1 nanomolar). Binding data 68 may be derived or received from a variety of sources, such as experimental measurements, computed estimates, expert insight, or presumption (for example, a random pair of molecule and protein are highly unlikely to bind).

Example 1

Construction of Experimental Benchmarks

The application of disclosed systems and methods is demonstrated on three benchmarks: the Directory of Useful Decoys Enhanced (DUDE) benchmark (see Mysinger et al., 2012, "Directory of useful decoys, enhanced (dud-e): Better ligands and decoys for better benchmarking," Journal of Medicinal Chemistry 55, no. 14, pp. 6582-6594, PMID: 22716043, which is hereby incorporated by reference); an internal DUDE-like benchmark; and a benchmark with experimentally-verified inactive molecules. Each of these benchmarks provides a different and complimentary assessment of the performance of the disclosed systems and methods. As the standard benchmark, DUDE permits direct comparisons to other structure-based binding affinity prediction systems. Unfortunately, DUDE is only specific a test set, without specifying a separate training set. By constructing our own DUDE-like benchmark, we ensure that there is no overlap between the training and test molecules. Correctly classifying experimentally verified active and inactive molecules is a challenging test because structurally similar molecules can have different labels. See Hu et al., "Systematic identification and classification of three-dimensional activity cliffs," Journal of Chemical Information and Modeling 52, no. 6, pp. 1490-1498, which is hereby incorporated by reference. Such cases are excluded from benchmarks using property-matched decoys because of the dissimilarity requirement in order to presume decoys are inactive.

The methodology of the DUDE benchmark is fully described by Mysinger et al., 2012, "Directory of useful decoys, enhanced (dud-e): Better ligands and decoys for better benchmarking," Journal of Medicinal Chemistry 55, no. 14, pp. 6582-6594, PMID: 22716043, which is hereby incorporated by reference. An internal benchmark was constructed similarly for this example. Briefly, both benchmarks are constructed by first gathering diverse sets of active molecules for a set of target proteins. Analog bias is mitigated by removing similar actives; similar actives are eliminated by first clustering the actives based on scaffold similarity, then selecting exemplary actives from each cluster. Then, each active molecule is paired with a set of property matched decoys (PMD). See Wallach and Lilien, 2011, "Virtual Decoy Sets for Molecular Docking Benchmarks," J Chem. Inf. and Model., 51, no. 2, pp. 196-202; and Wallach et al., 2011 "Normalizing molecular clocking rankings using virtually generated decoys," J. Chem. Inf. and Model., 51, no. 8, pp. 1817-1830, each of which is hereby incorporated by reference. PMD are selected to be similar to each other and to known actives with respect to some one-dimensional physico-chemical descriptors (e.g., molecular weight) while being topologically dissimilar based on some 2D fingerprints (e.g., ECFP which are described in Rogers and Hahn, "Extended-connectivity fingerprints," 2010, Journal of Chemical Information and Modeling 50, no. 5, pp. 742-754, which is hereby incorporated by reference in its entirety). The enforcement of the topological dissimilarity supports the assumption that the decoys are likely to be inactives because they are chemically different from any known active.

DUDE.

The DUDE is a well-known benchmark for structure-based virtual screening methods from the Shoichet Lab at UCSF. See Mysinger et al., 2012, "Directory of useful decoys, enhanced (dud-e): Better ligands and decoys for better benchmarking," Journal of Medicinal Chemistry, 55, no. 14, pp. 6582-6594, PMID: 22716043, which is hereby incorporated by reference. It consists of 102 targets, 22,886 actives (an average of 224 actives per target) and 50 PMD per active. Thirty targets were randomly selected as the test set and the remaining 72 targets were designated as the training set.

ChEMBL-20 PMD.

A DUDE-like dataset derived from ChEMBL version 20 (Bento et al., 2014, "The chembl bioactivity database: an update," Nucleic Acids Research 42, no. D1, pp. D1083-D1090, which is hereby incorporated by reference) was constructed. All activity measurements that passed the following filters were considered: (i) affinity units measured in IC50 or Ki and lower than 1 µM, (ii) target confidence greater or equal to 6, (iii) target has an annotated binding site in the scPDB database (Desaphy et al. 2014, "sc-pclb: a 3d-database of ligandable binding sites 10 years on," Nucleic Acids Research D399-404, which is hereby incorporated by reference) and resolution <2.5 Å, and (iv) ligands passed PAINS filters (Baell and Holloway, 2010, "New substructure filters for removal of pan assay interference compounds (pains) from screening libraries and for their exclusion in bioassays," Journal of Medicinal Chemistry 53, no. 7, pp. 2719-2740, which is hereby incorporated by reference) and promiscuity rules (Bruns and Watson, 2012, "Rules for identifying potentially reactive or promiscuous compounds," Journal of Medicinal Chemistry 55, no. 22, pp. 9763-9772). Following Mysinger et al., target affinities were grouped by their UniProt gene name prefix (Bruns and Watson, 2012 "Rules for identifying potentially reactive or promiscuous compounds," Journal of Medicinal Chemistry 55, no. 22, pp. 9763-9772, which is hereby incorporated by reference) and targets for which there were less than 10 active ligands were removed. This filtering process yielded a set of 123,102 actives and 348 targets. Second, each active was paired with a set of 30 PMD selected from the ZINC database (Irwin and Shoichet, 2005, "ZINC-a free database of commercially available compounds for virtual screening," J. Chem. Inf. Model. 45, no. 1, pp. 177-182, which is hereby incorporated by reference) similarly to Mysinger et al., 2012, "Directory of useful decoys, enhanced (dud-e): Better ligands and decoys for better benchmarking," Journal of Medicinal Chemistry 55, no. 14, pp. 6582-6594, PMID: 22716043, which is hereby incorporated by reference. Third, the data was partitioned into training, validation and testing sets by first clustering the active ligands for each target based on their Bemis-Murcko scaffolds (Bemis and Murcko, 1996, "The properties of known drugs. I. molecular frameworks," Journal of Medicinal Chemistry 39, no. 15, pp. 2887-2893) and choosing ligands that were at least 3 µM apart as the cluster exemplars. Clusters with less than 10 exemplars were discarded. Fourth, the test set was defined by randomly selecting 50 targets with their corresponding actives and decoys. Last, the training set was further partitioned over the clusters into 5-fold cross validation sets. The final dataset consists of 78,904 actives, 2,367,120 decoys, and 290 targets.

Experimentally Verified Inactives.

A limitation of benchmarks based on PMD is that they exclude decoys that are similar to actives molecules. This design decision is in place to support the assumption that the selected decoys are likely to be inactive without experimental validation. This enforced dissimilarity between actives and decoys means that PMD benchmarks lack some challenging cases where actives and inactive molecules are highly similar (Hu et al., 2012, "Systematic identification and classification of three-dimensional activity cliffs," Journal of Chemical Information and Modeling 52, no. 6, pp. 1490-1498, which is hereby incorporated by reference). Such challenging cases were included by substituting decoys with molecules that have been experimentally validated to be inactives. A benchmark similar to the ChEMBL-20 PMD one was constructed but PMD were replaced with inactive molecules. A molecule is defined here as inactive if its measured activity is higher than 30 µM. This resulted in a set of 78,904 actives, 363,187 inactives, and 290 targets which was partitioned into 3-fold cross-validation sets over the Bemis-Murcko clusters. Targets with less than then clusters were never assigned into a validation set. Hence, the number of targets in the validation sets was 149.

Structure-Based Deep-Convolutional Neural Network.

The network topology for the convolutional neural network 24 in this experiment (AtomNet) consisted of an input layer 26 followed by multiple 3D-convolutional 28 and a scorer 30 consisting of fully connected layers topped by a logistic-cost layer that assigns probabilities over the active and inactive classes. All units in hidden layers are implemented with the ReLU activation function (Nair and Hinton, 2010 "'Rectified linear units improve restricted Boltzmann machines'" in Proceedings of the 27th International Conference on Machine Learning (ICML-10), Jun. 21-24, 2010, Haifa, Israel, pp. 807-814, which is hereby incorporated by reference).

Input Representation.

The input layer 26 receives vectorized versions of 1 Å 3D grids placed over co-complexes of the target proteins (target objects 58) and small-molecules (training objects/test objects) that are sampled within the target's binding site. First, the binding site is defined using a flooding algorithm (See Hendlich et al., 1997, "Ligsite: automatic and efficient detection of potential small molecule-binding sites in proteins.," J. Mol. Graph. Model 15, no. 6, which is hereby incorporated by reference) seeded by a bound ligand annotated in the scPDB database (See Desaphy et al. 2014, "sc-pdb: a 3d-database of ligandable binding sites 10 years on," Nucleic Acids Research D399-404, which is hereby incorporated by reference). Second, the coordinates of the co-complexes are shifted to a three-dimensional Cartesian system originated at the center-of-mass of the binding site. Third, multiple poses within the binding site cavity are sampled. Fourth, the geometric data is cropped to fit within an appropriate bounding box. In this study a cube of 20 Å, centered at the origin, is used. Fifth, the input data is translated into a fixed-size grid with 1 Å spacing. Each grid cell holds a value that represents the presence of some basic structural features in that location. Basic structural features can vary from a simple enumeration of atom types to more complex protein-ligand descriptors such as SPLIF (Da and Kireev, "'Structural protein ligand interaction fingerprints (splif) for structure-based virtual screening: Method and benchmark study," 2014, Journal of Chemical Information and Modeling 54, no. 9, pp. 2555-2561), SIFt (Deng et al., 2004, "Structural interaction fingerprint (SIFt): a novel method for analyzing three-dimensional protein-ligand binding interactions," J. Med. Chem. 47, no 0.2, pp. 337-344) or APIF (Prez-Nueno, 2009 "Apif: A new interaction fingerprint based on atom pairs and its application to virtual screening," Journal of Chemical Information and Modeling 49, no. 5, pp. 1245-1260). Last, the 3D grid is unfolded into a 1D floating point vector.

Network Architecture.

The 3D convolutional layers 28 were implemented to support parameters such as filter size, stride and padding in a similar fashion to the implementation of Krizhevsky et al., 2012, "Imagenet classification with deep convolutional neural networks," in *Advances in Neural Information Processing Systems* 2, Pereira, Burges, Bottou, Weinberger, eds., pp. 1097-1105, Curran Associates, Inc. which is hereby incorporated by reference. The network architecture the convolutional neural network 24 consisted of an input layer 26 as described above, followed by four convolutional layers 28 of $128\times5^3$, $256\times3^3$, $256\times3^3$, $256\times3^3$ (number of filters×filter-dimension), and two fully-connected layers with 1024 hidden units each, topped by a logistic-regression cost layer over two activity classes.

Convolutional Neural Network 24 Training.

Training the convolutional neural network 24 was done using stochastic gradient descent with the AdaDelta adaptive learning method (Zeiler, 2012 "ADADELTA: an adaptive learning rate method," CoRR, vol. abs/1212.5701, which is hereby incorporated by reference), the back propagation algorithm (Rumelhart et al., 1988, "Neurocomputing: Foundations of research," ch. Learning Representations by Back-propagating Errors, pp. 696-699, Cambridge, Mass., USA: MIT Press, which is hereby incorporated by reference), and mini-batches of 768 examples per gradient step. No attempt was made to optimize meta-parameters except the limitation of fitting the model into a GPU memory. Training time was about a week on six Nvidia-K10 GPUs.

Baseline Method for Comparison.

Smina (See Koes et al., 2013 "Lessons learned in empirical scoring with smina from the csar2011 benchmarking exercise," Journal of Chemical Information and Modeling 53, no. 8, pp. 1893-1904, 2013, which is hereby incorporated by reference), a fork of AutoDock Vina (Trott and Olson, 2010 "Autodock vina: Improving the speed and accuracy of docking with a new scoring function, efficient optimization, and multithreading," Journal of Computational Chemistry 31, no. 2, pp. 455-461, which is hereby incorporated by reference), was used as a baseline for the structure-based evaluation. Smina implements an improved empirical scoring function and minimization routines over its predecessor and is freely available under the GPLv2 license.

Results.

The area under the receiver operating characteristic (AUC) and log AUC were used to report results over the three benchmarks. The AUC indicates classification (or ranked order) performance by measuring the area under the curve of true-positive rate versus the false-positive rate. An AUC value of 1.0 means perfect separation whereas a value of 0.5 implies random separation. Log AUC is a measurement similar to AUC that emphasizes early enrichment performance by putting more weight at the beginning of the curve so cases correctly classified at the top of the rank-ordered list contribute more to the score than later ones. Here, a logarithmic base of 10 was used, which means that the weight of the first 1% of the ranked results is equal to the weight of the next 10%. Because the nonlinearity of a log AUC value makes it hard to interpret, the area under the log-scaled random curve (0.14462) was subtracted from the log AUC to get an adjusted-log AUC (See Mysinger and Shoichet, 2010, "Rapid context-dependent ligand desolvation in molecular docking," Journal of Chemical Information and Modeling 50, no. 9, pp. 1561-1573, which is hereby incorporated by reference). Hence, positive adjusted log AUC values imply better than random performance whereas negative ones imply worse than random performance. For brevity, the adjusted-log AUC and log AUC are used interchangeably herein.

Table 2 and FIGS. 10 through 13 summarize the results across the three different benchmarks. The exemplary system and method of the present disclosure performs similarly on the ChEMBL-20-PMD and the DUDE benchmarks. The exemplary system and method of the present disclosure achieves a mean AUC 0.78 and a mean log AUC of 0.32 on ChEMBL-20-PMD and 0.8 and 0.33 on DUDE respectively. This similar performance is not surprising because the two benchmarks were constructed similarly.

Figure 10:
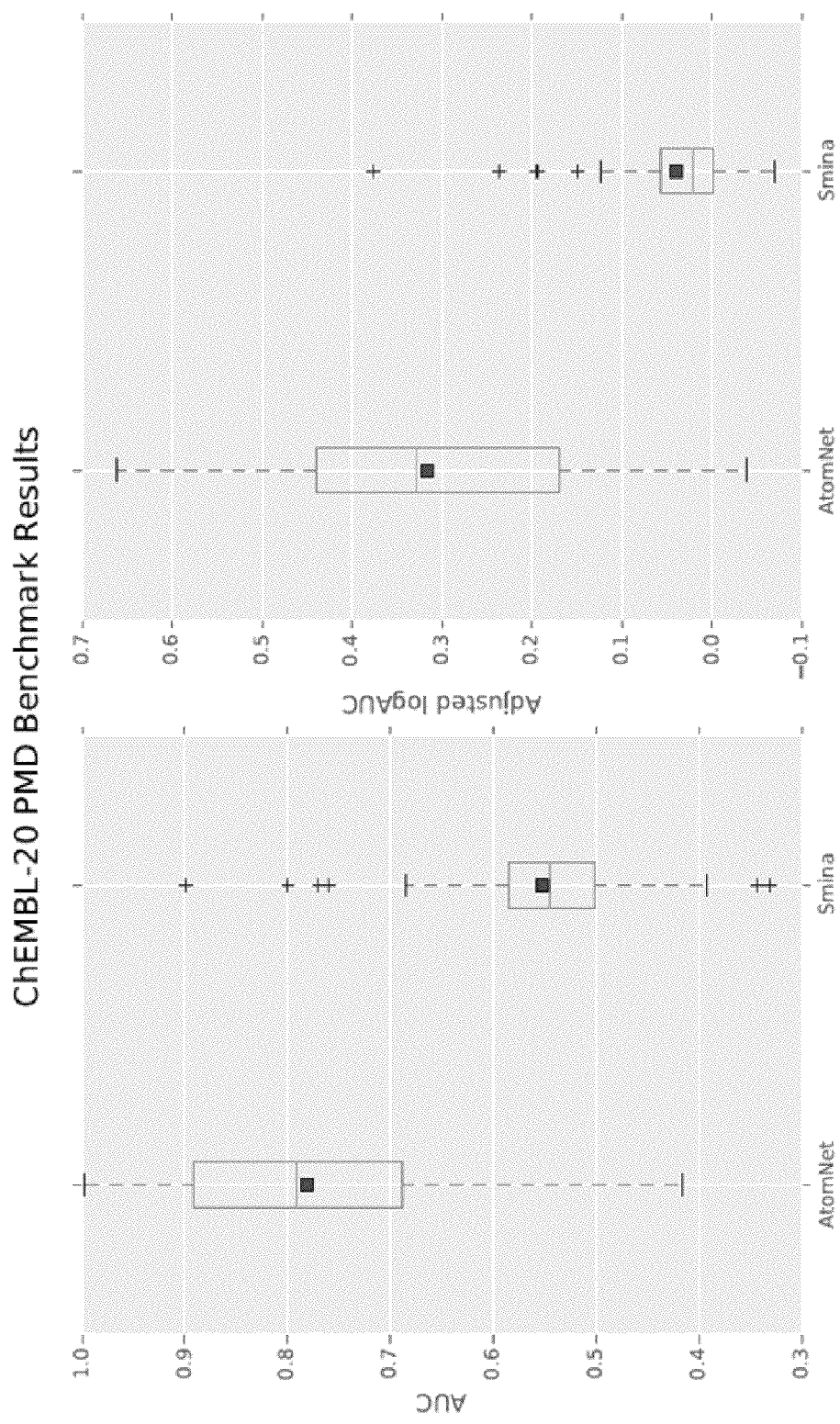
FIG. 10 illustrates a distribution of AUC and log AUC values of 50 ChEMBL-20-PMD targets for AtomNet and Smina according to an embodiment.
Figure 11:
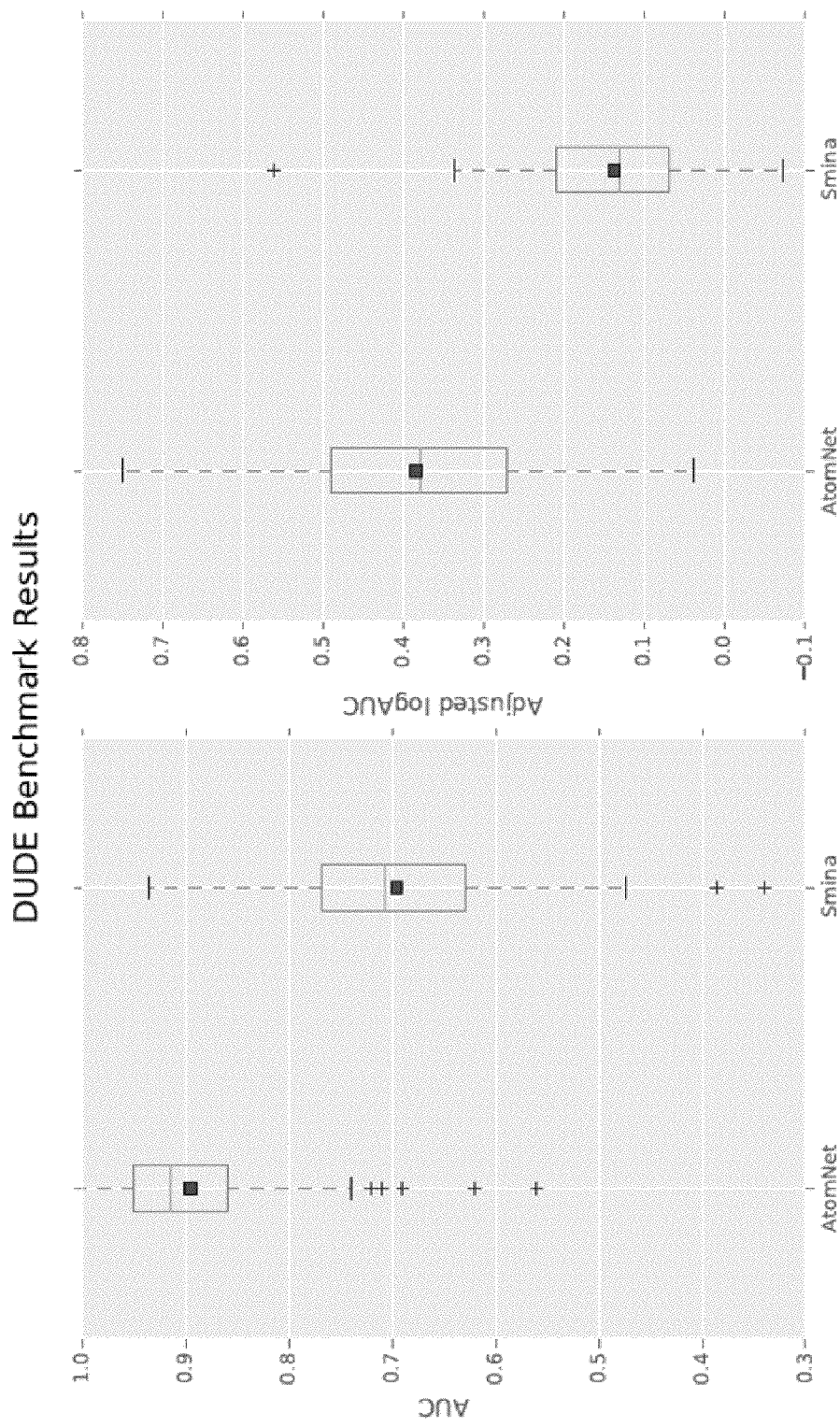
FIG. 11 illustrates the distribution of AUC and log AUC values of 102 DUDE targets for AtomNet and Smina according to an embodiment.
Figure 12:
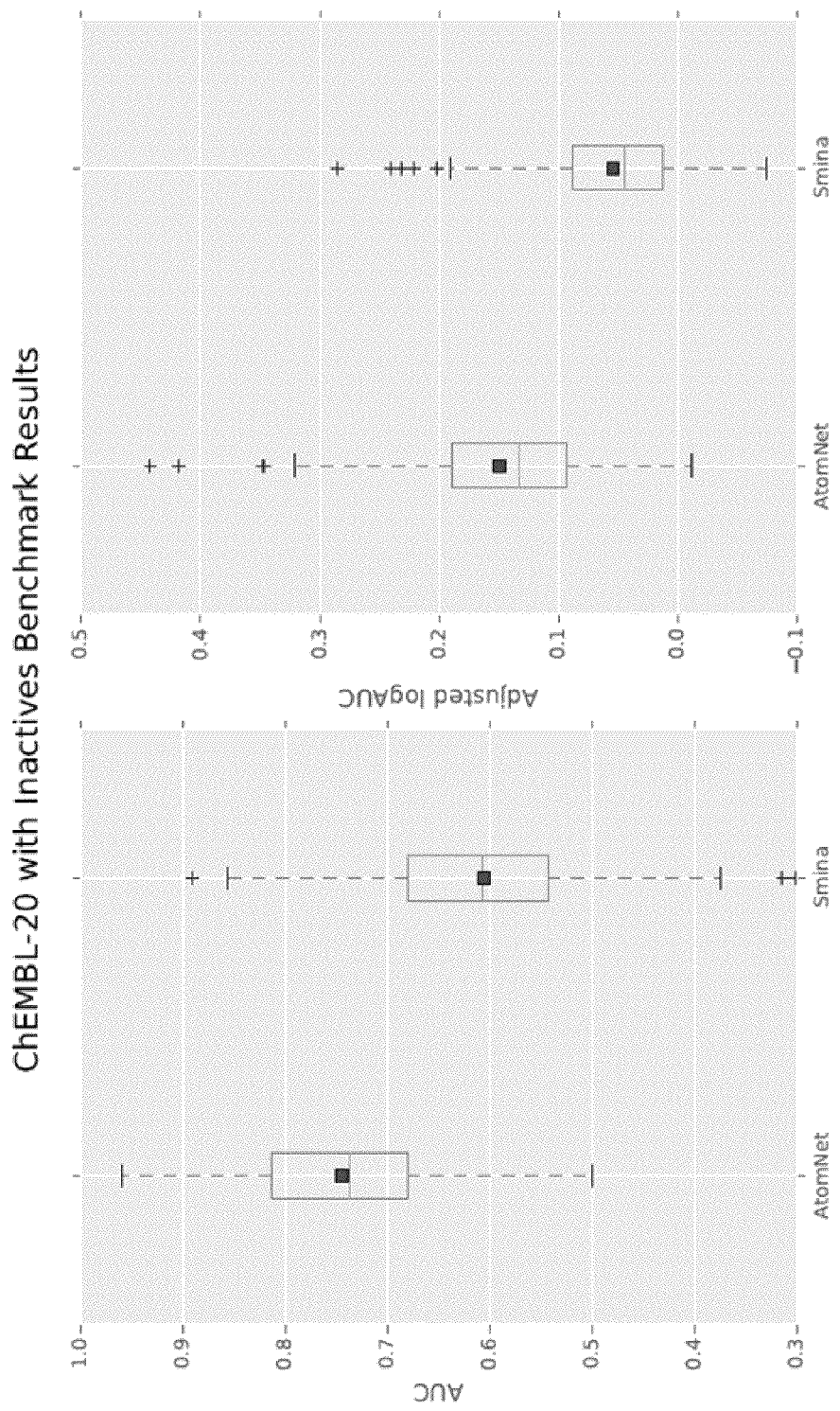
FIG. 12 illustrates the distribution of AUC and log AUC values of 149 ChEMBL-20-inactives targets for Atom-Net and Smina according to an embodiment.
Figure 13A:
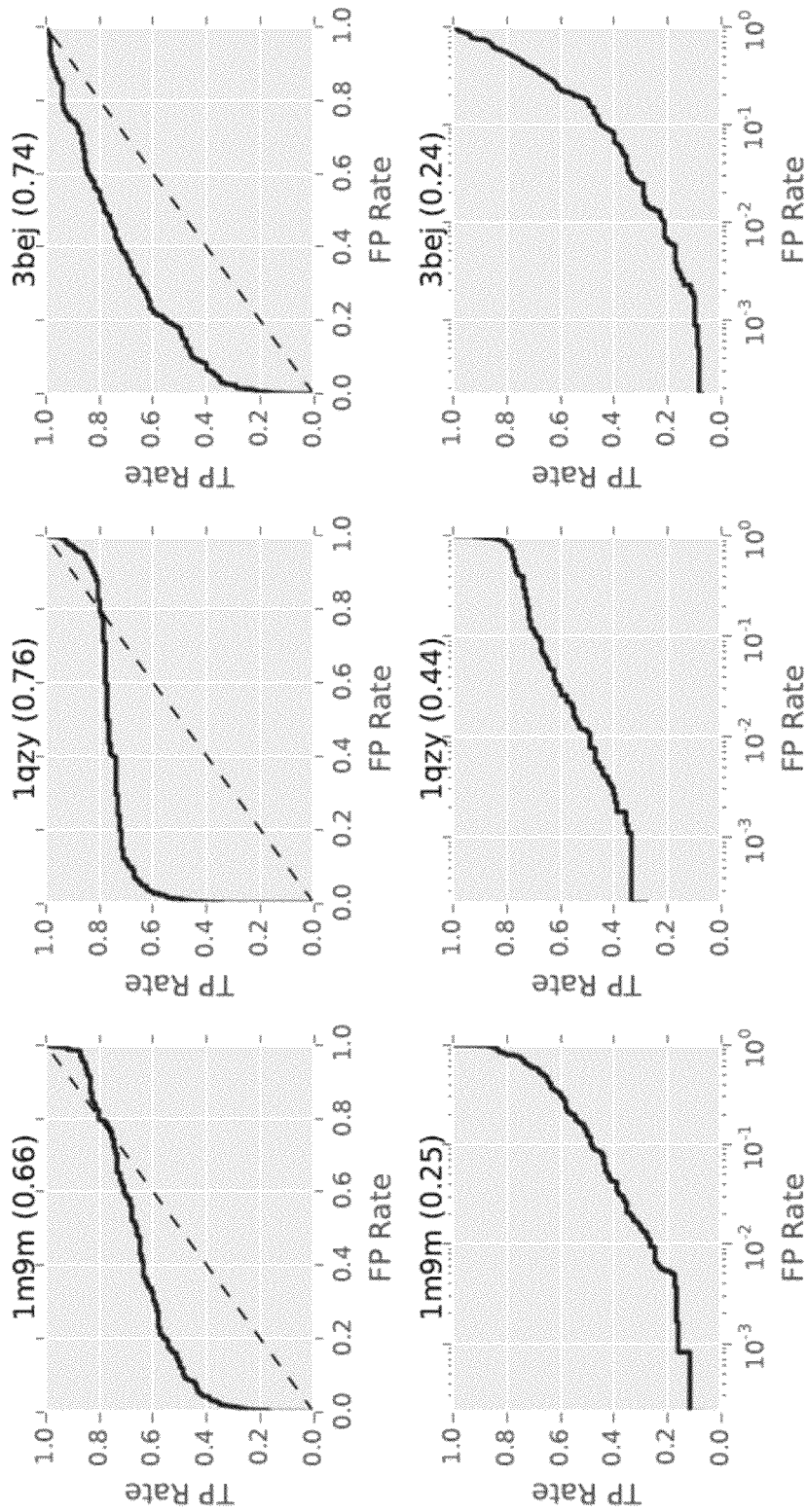
FIGS. 13A and 13B illustrate the differences between the AUC and log AUC measurements with respect to the early enrichment according to an embodiment.
Figure 13B:
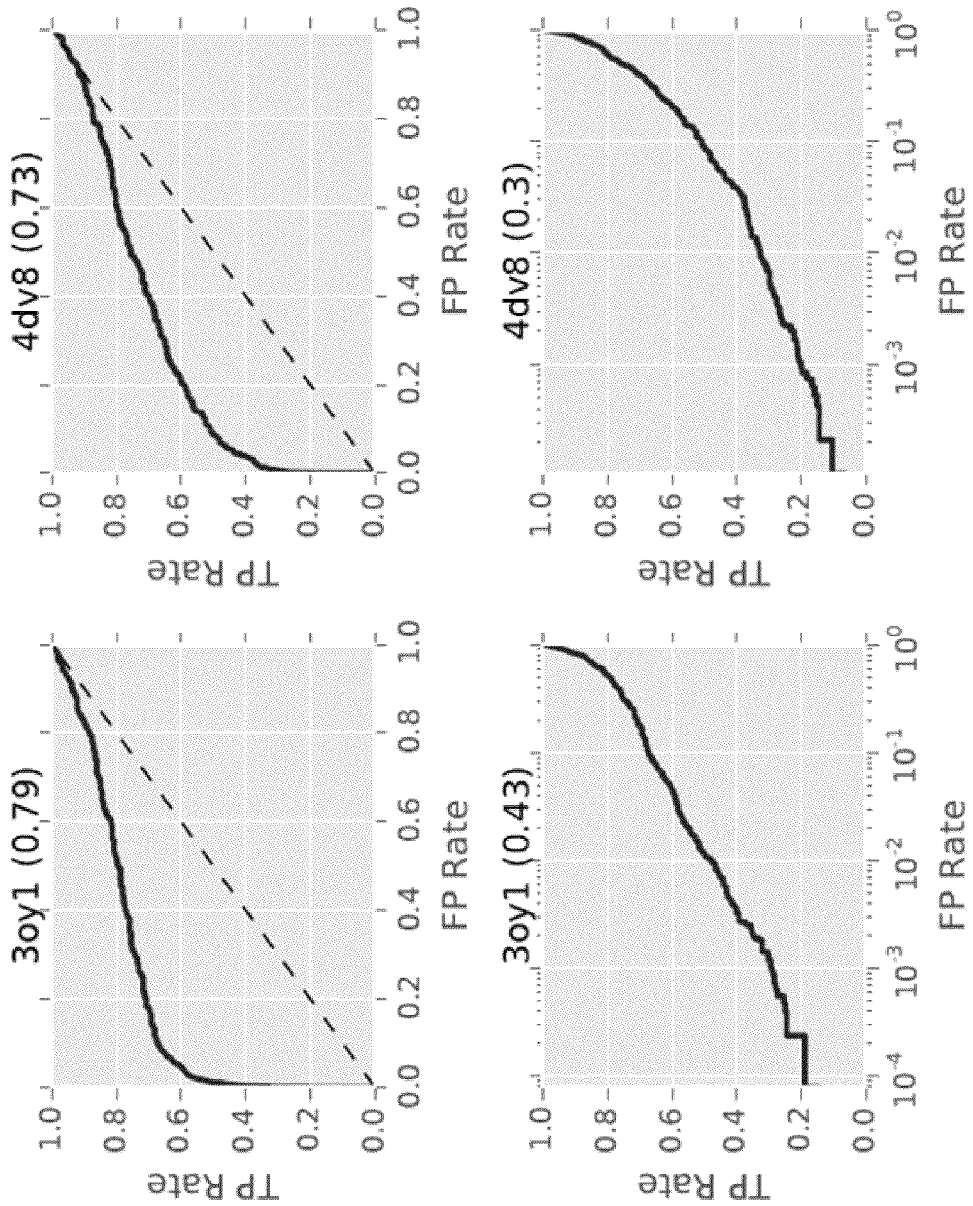

FIG. 10 provides the distribution of AUC and log AUC values of 50 ChEMBL-20-PMD targets for AtomNet and Smina. FIG. 11 provides the distribution of AUC and log AUC values of 102 DUDE targets for AtomNet and Smina. FIG. 12 provides the distribution of AUC and log AUC values of 149 ChEMBL-20-inactives targets for AtomNet and Smina. FIGS. 13A and 13B provide an illustration of the differences between the AUC and log AUC measurements with respect to the early enrichment.

TABLE 2

|  |  | AUC | | Adjusted logAUC | |
|---|---|---|---|---|---|
|  |  | Mean | Median | Mean | Median |
| ChEMBL-20 PMD | AtomNet | 0.781 | 0.792 | 0.317 | 0.328 |
|  | Smina | 0.552 | 0.544 | 0.04 | 0.021 |
| DUDE-30 | AtomNet | 0.855 | 0.875 | 0.321 | 0.355 |
|  | Smina | 0.7 | 0.694 | 0.153 | 0.139 |
| DUDE-102 | AtomNet | 0.895 | 0.915 | 0.385 | 0.38 |
|  | Smina | 0.696 | 0.707 | 0.138 | 0.132 |
| ChEMBL-20 inactives | AtomNet | 0.745 | 0.737 | 0.145 | 0.133 |
|  | Smina | 0.607 | 0.607 | 0.054 | 0.044 |

Table 2: Comparisons of AtomNet and Smina on the DUDE, ChEMBL-20-PMD, and ChEMBL-20-inactives benchmarks. DUDE-30 refers to the held-out set of 30 targets whereas DUDE-102 refers to the full dataset.

TABLE 3

|  | AUC | >0.5 | >0.6 | >0.7 | >0.8 | >0.9 |
|---|---|---|---|---|---|---|
| ChEMBL-20 PMD | AtomNet | 49 | 44 | 36 | 24 | 10 |
|  | Smina | 38 | 10 | 4 | 1 | 0 |
| DUDE-30 | AtomNet | 30 | 29 | 27 | 22 | 14 |
|  | Smina | 29 | 25 | 14 | 5 | 1 |
| DUDE-102 | AtomNet | 102 | 101 | 99 | 88 | 59 |
|  | Smina | 96 | 84 | 53 | 17 | 1 |
| ChEMBL-20 inactives | AtomNet | 149 | 136 | 105 | 45 | 10 |
|  | Smina | 129 | 81 | 31 | 4 | 0 |

Table 3: The number of targets on which AtomNet and Smina exceed given AUC thresholds. For example, on the CHEMBL-20 PMD set, AtomNet achieves an AUC of 0.8 or better for 24 targets (out of 50 possible targets). ChEMBL-20 PMD contains 50 targets, DUDE-30 contains 30 targets, DUDE-102 contains 102 targets, and ChEMBL-20 inactives contains 149 targets.

TABLE 4

|  | Adjusted-Log AUC | >0.0 | >0.1 | >0.2 | >0.3 | >0.4 |
|---|---|---|---|---|---|---|
| ChEMBL-20 PMD | AtomNet | 49 | 44 | 36 | 24 | 10 |
|  | Smina | 35 | 8 | 2 | 1 | 0 |
| DUDE-30 | AtomNet | 30 | 27 | 22 | 17 | 10 |
|  | Smina | 29 | 19 | 8 | 2 | 1 |
| DUDE-102 | AtomNet | 102 | 99 | 88 | 69 | 43 |
|  | Smina | 94 | 65 | 28 | 5 | 1 |
| ChEMBL-20 inactives | AtomNet | 147 | 107 | 36 | 10 | 2 |
|  | Smina | 123 | 35 | 5 | 0 | 0 |

Table 4: The number of targets on which AtomNet and Smina exceed given adjusted-log AUC thresholds. For example, on the CHEMBL-20 PMD set, AtomNet achieves an adjusted-log AUC of 0.3 or better for 27 targets (out of 50 possible targets). ChEMBL-20 PMD contains 50 targets, DUDE-30 contains 30 targets, DUDE-102 contains 102 targets, and ChEMBL-20 inactives contains 149 targets.

On each of our four evaluation data sets, the disclosed system and method (AtomNet) achieves an order-of-magnitude improvement over Smina at a level of accuracy useful for drug discovery. On the full DUDE set, AtomNet achieves or exceeds 0.9 AUC on 59 targets (or 57.8%). Smina only achieves 0.9 AUC for a single target (weel), approximately one percent of the benchmark. AtomNet achieves 0.8 or better AUC for 88 targets (86.3%), while Smina achieves it for 17 targets (16.7%). When the evaluation is restricted to the held-out 30 target subset of DUDE, AtomNet exceeds an AUC of 0.9 and 0.8 for 14 targets (46.7%) and 22 targets (73.3%), respectively. Smina achieves the same accuracy for one target (3.3°/o) and 5 targets (16.7%), respectively. AtomNet achieves mean and median AUC of 0.855 and 0.875 on the held-out set compared to 0.7 and 0.694 achieved by Smina, reducing available mean error by 51.6%. As expected, the performance of AtomNet drops slightly for its held-out examples whereas Smina's performance does not.

On the PMD dataset, AtomNet achieves an AUC of 0.9 or better for 10 held-out targets (20% of the set), while Smina achieves it on zero targets. When the standard of accuracy is reduced to an AUC of 0.8 or better, AtomNet succeeds on 25 targets (50°/o) while Smina only succeeds on 1 target (2%).

The third benchmark, which uses inactives instead of property-matched decoys, seems to be more challenging than the other two. AtomNet predicts with an AUC at or better than 0.9 for 10 targets (6.7%), while Smina succeeds at zero. For meeting or exceeding 0.8 AUC, AtomNet succeeds for 45 targets (30.2%) and Smina succeeds for 4 (2.70%). Although both Atomnet and Smina perform worse than on the previous benchmarks, AtomNet still significantly outperforms Smina with respect to overall and early enrichment performances. Because this benchmark uses inactives it includes challenging classification cases of structurally similar molecules with different labels (Hu et al., "Systematic identification and classification of three-dimensional activity cliffs," 2012, Journal of Chemical Information and Modeling 52, no. 6, pp. 1490-1498). These cases are excluded from benchmarks using PMD because decoys must be structurally dissimilar in order to presume they can be labeled as inactive.

Additionally AtomNet shows good early enrichment performance as indicated by the highly positive log AUC values. AtomNet outperforms Smina with respect to its early enrichment, achieving a mean log AUC of 0.321 compared to 0.153 of Smina. Visualizing the ROC curves illustrate the difference between the AUC and log AUC measurements with respect to the early enrichment. For example, FIG. 13A shows that the AUC value for target lm9m is 0.66 which may imply mediocre performance. However, the early enrichment indicated by the log AUC for that target is 0.25 which suggest that many actives are concentrated at the very top of the rank-ordered results. Similarly, target lqzy has an AUC value of 0.76 but log-BLscale plot suggest that 35% of its actives are concentrated at the very top of the rank-order list with log AUC of 0.44.

Discussion—Filter Visualization.

Figure 15A:
FIGS. 15A and 15B illustrates the three-dimensional locations on a target object at which a particular filter from a first convolutional layer fires in accordance with some embodiments.
Figure 15B:

Convolutional layers 28 consist of multiple different filters that learn to identify specific locally-related features by repeatedly applying these filters across the receptive field. When dealing with images, one can visualize these filters to verify that the model is capable of learning relevant features. For example, Krizhevsky et al., 2012, "Imagenet classification with deep convolutional neural networks," in *Advances in Neural Information Processing Systems* 2, Pereira, Burges, Bottou, Weinberger, eds., pp. 1097-1105, Curran Associates, Inc. which is hereby incorporated by reference, demonstrated that filters in the first convolutional layer of their model could detect lines, edges, and color gradients. In our case, however, the filters are not easily visualized because: (i) the filters are 3-dimensional, and (ii) the input channels are discrete. For example, two close RGB values will result with two similar colors but carbon is not closer to nitrogen than to oxygen. That is, similar values do not imply similar functionalities. To overcome these limitations an indirect approach is taken. Instead of directly visualizing filters in order to understand their specialization, filters are applied to input data and the location where they maximally fire is examined. Using this technique filters were mapped to chemical function. For example, visual inspection of the three-dimensional locations on the target object at which a particular filter from the first convolutional layer 28 fire reveals that this filter specializes as a sulfonyl/sulfonamide detector. See, for examples, FIGS. 15A and 15B which illustrate such an interaction. This demonstrates the ability of the model to learn complex chemical features from simpler ones. In this case, the filter has inferred a meaningful spatial arrangement of input atom types without any chemical prior knowledge.

Comparison to Other Structure-Based Methods.

This example provides an embodiment of the disclosed system and method for applying a deep convolutional neural network 24 to bioactivity predictions rather than reporting head-to-head comparisons to other structure-based methods. In order to put results in context, the popular program Smina was used as a baseline point of reference. Smina has practical advantages: it is fast, free, and under active development, so is suitable for analyzing large benchmarks in a timely and cost-efficient manner. Nevertheless, using published work, a broader context is provided by comparing AtomNet to other commercial docking algorithms reported in the literature. Like Smina, DUDE is publicly available and widely used. DUDE has certain limitations: for example, DUDE and other PMD benchmarks are inappropriate for the evaluation of ligand-based models (See Irwin, "Community benchmarks for virtual screening," 2008, J. Comput.-Aided Mol. Des. 22, no. 3-4, pp. 193-199, which is hereby incorporated by reference), because the same descriptors used to enforce diversity between actives and decoys are used to train ligand-base scorers. Further, as discussed earlier, absence of contamination between training and testing cannot be guaranteed when evaluating on DUDE, which was the main motivation for constructing the disclosed ChEMBL-20-PMD benchmark. However, the similar performance on these two benchmarks suggests that the results are robust. The following comparisons to previously described results are therefore presented: Gabel et at. (See Gabel et al., 2014 "Beware of machine learning-based scoring functions on the danger of developing black boxes," Journal of Chemical Information and Modeling 54, no. 10, pp. 2807-2815, which is hereby incorporated by reference) evaluated Surflex-Dock (See Spitzer and Jain, 2012 "Surftex-dock: Docking benchmarks and real-world application," Journal of Computer-Aided Molecular Design 26, no. 6, pp. 687-699, which is hereby incorporated by reference) on a representative set of 10 targets from the DUDE. The median AUC of Surfiex-Dock was 0.76 compared to 0.83 achieved by AtomNet. Coleman et al. (See Coleman et al., 2014, "Samp14 & dock3.7: lessons for automated docking procedures," Journal of Computer-Aided Molecular Design 28, no. 3, pp. 201-209, which is hereby incorporated by reference) evaluated DOCK-3.7 (Coleman et al., "Ligand pose and orientational sampling in molecular docking," *PLoS ONE* 8, p. e75992, which is hereby incorporated by reference) in a fully automated manner over the whole DUDE benchmark. They achieved mean AUC of 0.674 and log AUC of 0.164 compared to our AUC of 0.792 and log AUC of 0.306.

Conclusion.

The disclosed system and method presented in this example (AtomNet) is the first structure-based deep convolutional neural network designed to predict the bioactivity of small molecules for drug discovery applications. The locally-constrained deep convolutional architecture allows the system to model the complex non-linear phenomenon of molecular binding by hierarchically composing proximate basic chemical features into more intricate ones. By incorporating structural target information AtomNet can predict new active molecules even for targets with no previously known modulators. AtomNet shows outstanding results on a widely used structure-based benchmark achieving an AUC greater than 0.9 on 57.8% of the targets, 59 times as many targets as a widely-used docking method.

Example 2

Use Cases

The following are sample use cases provided for illustrative purposes only that describe some applications of some embodiments of the invention. Other uses may be considered, and the examples provided below are non-limiting and may be subject to variations, omissions, or may contain additional elements.

While each example below illustrates binding affinity prediction, the examples may be found to differ in whether the predictions are made over a single molecule, a set, or a series of iteratively modified molecules; whether the predictions are made for a single target or many, whether activity against the targets is to be desired or avoided, and whether the important quantity is absolute or relative activity; or, if the molecules or targets sets are specifically chosen (e.g., for molecules, to be existing drugs or pesticides; for proteins, to have known toxicities or side-effects).

Hit Discovery.

Pharmaceutical companies spend millions of dollars on screening compounds to discover new prospective drug leads. Large compound collections are tested to find the small number of compounds that have any interaction with the disease target of interest. Unfortunately, wet lab screening suffers experimental errors and, in addition to the cost and time to perform the assay experiments, the gathering of large screening collections imposes significant challenges through storage constraints, shelf stability, or chemical cost. Even the largest pharmaceutical companies have only between hundreds of thousands to a few millions of compounds, versus the tens of millions of commercially available molecules and the hundreds of millions of simulate-able molecules.

A potentially more efficient alternative to physical experimentation is virtual high throughput screening. In the same manner that physics simulations can help an aerospace engineer to evaluate possible wing designs before a model is physically tested, computational screening of molecules can focus the experimental testing on a small subset of high-likelihood molecules. This may reduce screening cost and time, reduces false negatives, improves success rates, and/or covers a broader swath of chemical space.

In this application, a protein target may be provided as input to the system. A large set of molecules may also be provided. For each molecule, a binding affinity is predicted against the protein target. The resulting scores may be used to rank the molecules, with the best-scoring molecules being most likely to bind the target protein. Optionally, the ranked molecule list may be analyzed for clusters of similar molecules; a large cluster may be used as a stronger prediction of molecule binding, or molecules may be selected across clusters to ensure diversity in the confirmatory experiments.

Off-Target Side-Effect Prediction.

Many drugs may be found to have side-effects. Often, these side-effects are due to interactions with biological pathways other than the one responsible for the drug's therapeutic effect. These off-target side-effects may be uncomfortable or hazardous and restrict the patient population in which the drug's use is safe. Off-target side effects are therefore an important criterion with which to evaluate which drug candidates to further develop. While it is important to characterize the interactions of a drug with many alternative biological targets, such tests can be expensive and time-consuming to develop and run. Computational prediction can make this process more efficient.

In applying an embodiment of the invention, a panel of biological targets may be constructed that are associated with significant biological responses and/or side-effects. The system may then be configured to predict binding against each protein in the panel in turn. Strong activity (that is, activity as potent as compounds that are known to activate the off-target protein) against a particular target may implicate the molecule in side-effects due to off-target effects.

Toxicity Prediction.

Toxicity prediction is a particularly-important special case of off-target side-effect prediction. Approximately half of drug candidates in late stage clinical trials fail due to unacceptable toxicity. As part of the new drug approval process (and before a drug candidate can be tested in humans), the FDA requires toxicity testing data against a set of targets including the cytochrome P450 liver enzymes (inhibition of which can lead to toxicity from drug-drug interactions) or the hERG channel (binding of which can lead to QT prolongation leading to ventricular arrhythmias and other adverse cardiac effects).

In toxicity prediction, the system may be configured to constrain the off-target proteins to be key antitargets (e.g. CYP450, hERG, or $5-HT_{2B}$ receptor). The binding affinity for a drug candidate may then predicted against these proteins. Optionally, the molecule may be analyzed to predict a set of metabolites (subsequent molecules generated by the body during metabolism/degradation of the original molecule), which can also be analyzed for binding against the antitargets. Problematic molecules may be identified and modified to avoid the toxicity or development on the molecular series may be halted to avoid wasting additional resources.

Potency Optimization.

One of the key requirements of a drug candidate is strong binding against its disease target. It is rare that a screen will find compounds that bind strongly enough to be clinically effective. Therefore, initial compounds seed a long process of optimization, where medicinal chemists iteratively modify the molecular structure to propose new molecules with increased strength of target binding. Each new molecule is synthesized and tested, to determine whether the changes successfully improved binding. The system may be configured to facilitate this process by replacing physical testing with computational prediction.

In this application, the disease target and a set of lead molecules may be input into the system. The system may be configured to produce binding affinity predictions for the set of leads. Optionally, the system could highlight differences between the candidate molecules that could help inform the reasons for the predicted differences in binding affinity. The medicinal chemist user can use this information to propose a new set of molecules with, hopefully, improved activity against the target. These new alternative molecules may be analyzed in the same manner.

Selectivity Optimization.

As discussed above, molecules tend to bind a host of proteins at a variety of strengths. For example, the binding pockets of protein kinases (which are popular chemotherapy targets) are very similar and most kinase inhibitors affect many different kinases. This means that various biological pathways are simultaneously modified, which yields a "dirty" medicinal profile and many side-effects. The critical challenge in the design of many drugs, therefore, is not activity per se but specificity: the ability to selectively target one protein (or a subset of proteins) out from a set of possibly-closely related proteins.

Our system can reduce the time and cost of optimizing the selectivity of a candidate drug. In this application, a user may input two sets of proteins. One set describes proteins against which the compound should be active, while the other set describes proteins against which the compound should be inactive. The system may be configured to make predictions for the molecule against all of the proteins in both sets, establishing a profile of interaction strengths. Optionally, these profiles could be analyzed to suggest explanatory patterns in the proteins. The user can use the information generated by the system to consider structural modifications to a molecule that would improve the relative binding to the different protein sets, and to design new candidate molecules with better specificity. Optionally, the system could be configured to highlight differences between the candidate molecules that could help inform the reasons for the predicted differences in selectivity. The proposed candidates can be analyzed iteratively, to further refine the specificity of their activity profiles.

Fitness function for automated molecular design: Automated tools to perform the preceding optimizations are valuable. A successful molecule requires optimization and balance among potency, selectivity, and toxicity. "Scaffold hopping" (when the activity of a lead compound is preserved but the chemical structure is significantly altered) can yield improved pharmacokinetics, pharmacodynamics, toxicity, or intellectual property profiles. Algorithms exist to iteratively suggest new molecules, such as random generation of molecules, growth of molecular fragments to fill a given binding site, genetic algorithms to "mutate" and "cross-breed" a population of molecules, and swapping of pieces of a molecule with bioisosteric replacements. The drug candidates generated by each of these methods must be evaluated against the multiple objectives described above (potency, selectivity, toxicity) and, in the same way that the technology can be informative on each of the preceding manual settings (binding prediction, selectivity, side-effect and toxicity prediction), it can be incorporated in an automated molecular design system.

Drug Repurposing.

All drugs have side-effects and, from time to time, these side-effects are beneficial. The best known example might be aspirin, which is generally used as a headache treatment but is also taken for cardiovascular health. Drug repositioning can significantly reduce the cost, time, and risk of drug discovery because the drugs have already been shown to be safe in humans and have been optimized for rapid absorption and favorable stability in patients. Unfortunately, drug repositioning has been largely serendipitous. For example, sildenafil (Viagra), was developed as a hypertension drug and was unexpectedly observed to be an effective treatment for erectile dysfunction. Computational prediction of off-target effects can be used in the context of drug repurposing to identify compounds that could be used to treat alternative diseases.

In this application, as in off-target side-effect prediction, the user may assemble a set of possible target proteins, where each protein is linked to a disease. That is, inhibition of each protein would treat a (possibly different) disease; for example, inhibitors of Cyclooxygenase-2 can provide relief from inflammation, whereas inhibitors of Factor Xa can be used as anticoagulants. These proteins are annotated with the binding affinity of approved drugs, if any exist. We then assemble a set of molecules, restricting the set to molecules that have been approved or investigated for use in humans. Finally, for each pair of protein and molecule, the user may use the system to predict the binding affinity. Candidates for drug repurposing may be identified if the predicted binding affinity of the molecule is close to the binding affinity of effective drugs for the protein.

Drug Resistance Prediction.

Drug resistance is an inevitable outcome of pharmaceutical use, which puts selection pressure on rapidly dividing and mutating pathogen populations. Drug resistance is seen in such diverse disease agents as viruses (HIV), exogenous microorganisms (MRSA), and disregulated host cells (cancers). Over time, a given medicine will become ineffective, irrespective of whether the medicine is antibiotics or chemotherapies. At that point, the intervention can shift to a different medicine that is, hopefully, still potent. In HIV, there are well-known disease progression pathways that are defined by which mutations the virus will accumulate while the patient is being treated.

There is considerable interest in predicting how disease agents adapt to medical intervention. One approach is to characterize which mutations will occur in the disease agent while under treatment. Specifically, the protein target of a medicine needs to mutate so as to avoid binding the drug while simultaneously continue to bind its natural substrate.

In this application, a set of possible mutations in the target protein may be proposed. For each mutation, the resulting protein shape may be predicted. For each of these mutant protein forms, the system may be configured to predict a binding affinity for both the natural substrate and the drug. The mutations that cause the protein to no longer bind to the drug but also to continue binding to the natural substrate are candidates for conferring drug resistance. These mutated proteins may be used as targets against which to design drugs, e.g. by using these proteins as inputs to one of these other prediction use cases.

Personalized Medicine.

Ineffective medicines should not be administered. In addition to the cost and hassle, all medicines have side-effects. Moral and economic considerations make it imperative to give medicines only when the benefits outweigh these harms. It may be important to be able to predict when a medicine will be useful. People differ from one another by a handful of mutations. However, small mutations may have profound effects. When these mutations occur in the disease target's active (orthosteric) or regulatory (allosteric) sites, they can prevent the drug from binding and, therefore, block the activity of the medicine. When a particular person's protein structure is known (or predicted), the system can be configured to predict whether a drug will be effective or the system may be configured to predict when the drug will not work.

For this application, the system may be configured to receive as input the drug's chemical structure and the specific patient's particular expressed protein. The system may be configured to predict binding between the drug and the protein and, if the drug's predicted binding affinity that particular patient's protein structure is too weak to be clinically effective, clinicians or practitioners may prevent that drug from being fruitlessly prescribed for the patient.

Drug Trial Design.

This application generalizes the above personalized medicine use case to the case of patient populations. When the system can predict whether a drug will be effective for a particular patient phenotype, this information can be used to help design clinical trials. By excluding patients whose particular disease targets will not be sufficiently affected by a drug, a clinical trial can achieve statistical power using fewer patients. Fewer patients directly reduces the cost and complexity of clinical trials.

For this application, a user may segment the possible patient population into subpopulations that are characterized by the expression of different proteins (due to, for example, mutations or isoforms). The system may be configured to predict the binding strength of the drug candidate against the different protein types. If the predicted binding strength against a particular protein type indicates a necessary drug concentration that falls below the clinically-achievable in-patient concentration (as based on, for example, physical characterization in test tubes, animal models, or healthy volunteers), then the drug candidate is predicted to fail for that protein subpopulation. Patients with that protein may then be excluded from a drug trial.

Agrochemical Design.

In addition to pharmaceutical applications, the agrochemical industry uses binding prediction in the design of new pesticides. For example, one desideratum for pesticides is that they stop a single species of interest, without adversely impacting any other species. For ecological safety, a person could desire to kill a weevil without killing a bumblebee.

For this application, the user could input a set of protein structures, from the different species under consideration, into the system. A subset of proteins could be specified as the proteins against which to be active, while the rest would be specified as proteins against which the molecules should be inactive. As with previous use cases, some set of molecules (whether in existing databases or generated de novo) would be considered against each target, and the system would return the molecules with maximal effectiveness against the first group of proteins while avoiding the second.

Materials Science.

To predict the behavior and properties of new materials, it may be useful to analyze molecular interactions. For example, to study solvation, the user may input a repeated crystal structure of a given small molecule and assess the binding affinity of another instance of the small molecule on the crystal's surface. To study polymer strength, a set of polymer strands may be input analogously to a protein target structure, and an oligomer of the polymer may be input as a small molecule. Binding affinity between the polymer strands may therefore be predicted by the system.

In one specific example, the system may be used to predict the strength of a material such as Kevlar by, e.g., predicting the strength of hydrogen bonds and pi-bond stacks. So, binding affinity prediction as disclosed herein may be used to facilitate the development of improved materials such as KEVLAR.

Simulation.

Simulators often measure the binding affinity of a molecule to a protein, because the propensity of a molecule to stay in a region of the protein is correlates to its binding affinity there. An accurate description of the features governing binding could be used to identify regions and poses that have particularly high or low binding energy. The energetic description can be folded into Monte Carlo simulations to describe the motion of a molecule and the occupancy of the protein binding region. Similarly, stochastic simulators for studying and modeling systems biology could benefit from an accurate prediction of how small changes in molecule concentrations impact biological networks.

CONCLUSION

The foregoing description, for purpose of explanation, has been described with reference to specific implementations. However, the illustrative discussions above are not intended to be exhaustive or to limit the implementations to the precise forms disclosed. Many modifications and variations are possible in view of the above teachings. The implementations were chosen and described in order to best explain the principles and their practical applications, to thereby enable others skilled in the art to best utilize the implementations and various implementations with various modifications as are suited to the particular use contemplated.

What is claimed is:

1. A computer system for characterization of a test object using spatial data, the computer system comprising:
   a graphical processing unit having a graphical processing memory;
   a general processor; and
   general memory addressable by the general processing unit, the general memory storing at least one program for execution by the at least one general processor, the at least one program comprising instructions for:
   (A) obtaining spatial coordinates for a target object;
   (B) modeling the test object with the target object in each pose of a plurality of different poses, thereby creating a plurality of voxel maps, wherein each respective voxel map in the plurality of voxel maps comprises the test object in a respective pose in the plurality of different poses;
   (C) unfolding each voxel map in the plurality of voxel maps into a corresponding vector, thereby creating a plurality of vectors, wherein each vector in the plurality of vectors is the same size;
   (D) providing the plurality of vectors to the graphical processing unit memory, wherein the graphical processing memory comprises a network architecture that includes an input layer for sequentially receiving the plurality of vectors, a plurality of convolutional layers, and a scorer, wherein
   the plurality of convolutional layers includes an initial convolutional layer and a final convolutional layer, each layer in the plurality of convolutional layers is associated with a different set of weights,
   responsive to input of a respective vector in the plurality of vectors, the input layer feeds a first plurality of values into the initial convolutional layer as a first function of values in the respective vector, wherein the first function is computed using the graphical processing unit,
   each respective convolutional layer, other than the final convolutional layer, feeds intermediate values, as a respective second function of (i) the different set of weights associated with the respective convolutional layer and (ii) input values received by the respective convolutional layer, into another convolutional layer in the plurality of convolutional layers, wherein the second function is computed using the graphical processing unit, and
   the final convolutional layer feeds final values, as a third function of (i) the different set of weights associated with the final convolutional layer and (ii) input values received by the final convolutional layer that is computed using the graphical processing unit, into the scorer;
   (E) obtaining a plurality of scores from the scorer, wherein each score in the plurality of scores corresponds to the input of a vector in the plurality of vectors into the input layer; and
   (F) using the plurality of scores to characterize the test object.

2. The computer system of claim 1, wherein the scorer comprises a plurality of fully-connected layers and an evaluation layer wherein a fully-connected layer in the plurality of fully-connected layers feeds into the evaluation layer.

3. The computer system of claim 1, wherein the scorer comprises a decision tree, a multiple additive regression tree, a clustering algorithm, principal component analysis, a nearest neighbor analysis, a linear discriminant analysis, a quadratic discriminant analysis, a support vector machine, an evolutionary method, a projection pursuit, and ensembles thereof.

4. The computer system of claim 1, wherein each vector in the plurality of vectors is a one-dimensional vector.

5. The computer system of claim 1, wherein the plurality of different poses comprises 2 or more poses, 10 or more poses, 100 or more poses, or 1000 or more poses.

6. The computer system of claim 1, wherein the plurality of different poses is obtained using a docking scoring function in one of markup chain Monte Carlo sampling, simulated annealing, Lamarckian Genetic Algorithms, or genetic algorithms.

7. The computer system of claim 1, wherein the plurality of different poses is obtained by incremental search using a greedy algorithm.

8. The computer system of claim 1, wherein the target object is a polymer.

9. The computer system of claim 8, wherein the polymer is a protein, a polypeptide, a polynucleic acid, a polyribonucleic acid, a polysaccharide, or an assembly of any combination thereof.

10. The computer system of claim 1, wherein the target object is a polymer and the spatial coordinates are a set of three-dimensional coordinates $\{x_1, \ldots, x_N\}$ for a crystal structure of the polymer resolved at a resolution of 2.5 Å or better.

11. The computer system of claim 1, wherein the target object is a polymer and the spatial coordinates are a set of three-dimensional coordinates $\{x_1, \ldots, x_N\}$ for a crystal structure of the polymer resolved at a resolution of 3.3 Å or better.

12. The computer system of claim 1, wherein the target object is a polymer and the spatial coordinates are an ensemble of three-dimensional coordinates for the polymer determined by nuclear magnetic resonance, neutron diffraction, or cryo-electron microscopy.

13. The computer system of claim 1, wherein the test object is a chemical compound and using the plurality of scores to characterize the test object comprises taking a measure of central tendency of the plurality of scores, wherein when the measure of central tendency satisfies a predetermined threshold value or predetermined threshold value range, the test object is deemed to have a first classification, and when the measure of central tendency fails to satisfy the predetermined threshold value or predetermined threshold value range, the test object is deemed to have a second classification.

14. The computer system of claim 1, wherein the using the plurality of scores to characterize the test object comprises taking a weighted average of the plurality of scores, wherein when the weighted average satisfies a predetermined threshold value or predetermined threshold value range, the test object is deemed to have a first classification, and when the weighted average fails to satisfy the predetermined threshold value or predetermined threshold value range, the test object is deemed to have a second classification.

15. The computer system of claim 14 wherein the weighted average is a Boltzman average of the plurality of scores.

16. The computer system of claim 14, wherein
the first classification is an $IC_{50}$, $EC_{50}$, Kd, or KI for the test object with respect to the target object that is above a first binding value, and
the second classification is an $IC_{50}$, $EC_{50}$, Kd, or KI for the test object with respect to the target object that is below the first binding value.

17. The computer system of claim 16 wherein the first binding value is one micromolar.

18. The computer system of claim 16 wherein the first binding value is ten micromolar.

19. The computer system of claim 16 wherein the first binding value is the predicted $IC_{50}$, $EC_{50}$, Kd, or KI for a different test object with respect to the target object.

20. The computer system of claim 1, wherein the using the plurality of scores to characterize the test object comprises taking a weighted average of the plurality of scores, wherein when the weighted average satisfies a respective threshold value range in a plurality of threshold value ranges, the test object is deemed to have a respective classification in a plurality of a respective classifications that uniquely corresponds to the respective threshold value range.

21. The computer system of claim 20, wherein each respective classification in the plurality of classifications is an $IC_{50}$, $EC_{50}$, Kd, or KI range for the test object with respect to the target object.

22. The computer system of claim 21, wherein a first classification in the plurality of classifications is between one micromolar and ten micromolar.

23. The computer system of claim 21, wherein a first classification in the plurality of classifications is between one nanomolar and 100 nanomolar.

24. The computer system of claim 1, wherein the target object is a polymer with an active site, the test object is a chemical composition, and the modeling comprises docking the test object into the active site of the polymer.

25. The computer system of claim 1, wherein a convolutional layer in the plurality of convolutional layers has a plurality of filters and wherein each filter in the plurality of filters convolves a cubic input space of $N^3$ with stride Y, where N is an integer of two or greater and Y is a positive integer.

26. The computer system of claim 25, wherein the different set of weights associated with the convolutional layer are associated with respective filters in the plurality of filters.

27. The computer system of claim 1, wherein the scorer comprises a plurality of fully-connected layers and a logistic regression cost layer wherein a fully-connected layer in the plurality of fully-connected layers feeds into the logistic regression cost layer.

28. The computer system of claim 1, wherein the scorer comprises a decision tree, a multiple additive regression tree, a clustering algorithm, principal component analysis, a nearest neighbor analysis, a linear discriminant analysis, a quadratic discriminant analysis, a support vector machine, an evolutionary method, a projection pursuit, or ensembles thereof.

29. The computer system of claim 1, wherein
the target object is a polymer with an active site,
the test object is a chemical composition,
the modeling comprises performing a molecular dynamics run of the target object and the test object thereby forming a trajectory of the target object and the test object together over time, and
a subset of the plurality of different poses is obtained by taking snapshots of the trajectory over a period of time.

* * * * *